(12) United States Patent
Fitzgerald

(10) Patent No.: US 7,314,632 B1
(45) Date of Patent: Jan. 1, 2008

(54) ***PSEUDOMONAS* EXOTOXIN A-LIKE CHIMERIC IMMUNOGENS**

(75) Inventor: David J. Fitzgerald, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/462,682

(22) PCT Filed: Jul. 10, 1998

(86) PCT No.: PCT/US98/14341

§ 371 (c)(1),
(2), (4) Date: Apr. 28, 2000

(87) PCT Pub. No.: WO99/02713

PCT Pub. Date: Jan. 21, 1999

Related U.S. Application Data

(60) Provisional application No. 60/052,375, filed on Jul. 11, 1997.

(51) Int. Cl.
*A61K 39/108* (2006.01)
(52) U.S. Cl. .............. 424/236.1; 424/260.1; 424/190.1; 424/133.1; 424/183.1; 424/184.1; 424/192.1; 424/193.1; 530/350
(58) Field of Classification Search .......... 424/134.1, 424/185.1, 178.1, 183.1, 282.1, 194, 179.1, 424/832, 236.1, 260.1, 190.1, 184.1, 192.1, 424/193.1, 252.33, 261; 530/350, 324, 391.7, 530/351, 387.3, 356, 387.7, 387.1, 399, 391.1, 530/300, 536; 538/825; 435/69.7, 5, 252.33, 435/69.1, 71.1; 514/12
See application file for complete search history.

(56) References Cited

U.S. PATENT DOCUMENTS

| | | | | |
|---|---|---|---|---|
| 4,545,985 A | * | 10/1985 | Pastan et al. | 424/180.1 |
| 4,892,827 A | * | 1/1990 | Pastan et al. | 435/193 |
| 4,958,009 A | * | 9/1990 | Bjorn et al. | 424/183.1 |
| 5,082,927 A | * | 1/1992 | Pastan et al. | 530/351 |
| 5,190,873 A | * | 3/1993 | Lernhardt et al. | 435/177 |
| 5,206,353 A | * | 4/1993 | Berger et al. | 536/23.4 |
| 5,328,984 A | * | 7/1994 | Pastan et al. | 424/134.1 |

(Continued)

FOREIGN PATENT DOCUMENTS

EP 0583794 * 9/1987

(Continued)

OTHER PUBLICATIONS

Ashorn, Per et al, Proc. Nat'l Acad. Sci, (USA), vol. 87, p. 8889-8893, Nov. 1990.*

(Continued)

*Primary Examiner*—Mark Navarro
*Assistant Examiner*—Ginny Allen Portner
(74) *Attorney, Agent, or Firm*—Townsend and Townsend and Crew LLP

(57) ABSTRACT

This invention provides *Pseudomonas* exotoxin A-like chimeric immunogens that include a non-native epitope in the Ib domain of *Pseudomonas* exotoxin. Methods of eliciting an immune response using these immunogens also are provided.

12 Claims, 14 Drawing Sheets

1A  Pseudomonas exotoxin    1B  V3-loop toxin chimera

1C

| Protein | Ib Loop Region Amino Acid Sequence | Molecular Mass |
|---|---|---|
| wild-type PE | -GAANADVVSLTCPVAAGECAGPAD- | 67,122 Da |
| ntPE-V3MN14 | -GAAN*LH*CGIHIGPGRAFYTTKCMQGPAD- | 67,729 Da |
| ntPE-V3MN26 | -GAAN*LH*CNYNKRKRIHIGPGRAFYT TKNIIGTICMQGPAD- | 68,937 Da |
| ntPE-V3ThB26 | -GAAN*LH*CSNNTRTSITIGPGQVFYRT GDIIGDDICMQGPAD- | 68,700 Da |
| ntPE-FP16 | -GAAN*LQ*CRLEEKKGNYVVTDHRLCLQGPAD- | 67,862 Da |

U.S. PATENT DOCUMENTS

| | | | | |
|---|---|---|---|---|
| 5,428,143 | A | * | 6/1995 | Berger et al. ............... 536/23.4 |
| 5,458,878 | A | * | 10/1995 | Pastan et al. ............ 424/260.1 |
| 5,512,658 | A | * | 4/1996 | Pastan et al. ............... 530/350 |
| 5,573,916 | A | | 11/1996 | Cheronis et al. |
| 5,587,455 | A | * | 12/1996 | Berger et al. ............... 530/324 |
| 5,602,095 | A | * | 2/1997 | Pastan et al. .................. 514/12 |
| 5,608,039 | A | * | 3/1997 | Pastan et al. ............ 530/387.3 |
| 5,612,036 | A | * | 3/1997 | Hodges et al. ........... 424/190.1 |
| 5,696,237 | A | * | 12/1997 | FitzGerald et al. ...... 530/387.3 |
| 5,705,156 | A | * | 1/1998 | Pastan et al. ............ 424/183.1 |
| 5,705,163 | A | | 1/1998 | Pastan et al. |
| 5,821,238 | A | * | 10/1998 | Pastan et al. ............ 424/134.1 |
| 5,843,882 | A | * | 12/1998 | Boyd et al. ..................... 514/2 |
| 5,854,044 | A | * | 12/1998 | Pastan et al. ............... 435/194 |
| 5,863,745 | A | * | 1/1999 | Fitzgerald et al. ......... 435/7.21 |
| 5,869,045 | A | | 2/1999 | Hellstrom et al. |
| 5,935,580 | A | * | 8/1999 | Ladant et al. ............ 424/192.1 |
| 5,965,406 | A | * | 10/1999 | Murphy ..................... 435/69.7 |
| 5,980,895 | A | * | 11/1999 | Pastan et al. ............ 424/178.1 |
| 5,980,896 | A | | 11/1999 | Hellstrom et al. |
| 5,990,296 | A | * | 11/1999 | Pastan et al. ............ 536/23.53 |
| 6,011,002 | A | * | 1/2000 | Pastan et al. .................. 514/2 |
| 6,020,145 | A | | 2/2000 | Hellstrom et al. |
| 6,022,950 | A | * | 2/2000 | Murphy ..................... 530/350 |
| 6,051,405 | A | * | 4/2000 | FitzGerald et al. ......... 435/69.7 |
| 6,074,644 | A | * | 6/2000 | Pastan et al. ............ 424/178.1 |
| 6,083,502 | A | * | 7/2000 | Pastan et al. ............ 424/178.1 |
| 6,086,900 | A | * | 7/2000 | Draper .................... 424/282.1 |
| 6,090,388 | A | * | 7/2000 | Wang ...................... 424/185.1 |
| 6,099,842 | A | * | 8/2000 | Pastan et al. ............ 424/183.1 |
| 6,140,066 | A | | 10/2000 | Lorberboum-Galski et al. |
| 6,146,631 | A | * | 11/2000 | Better et al. ............. 424/183.1 |
| 6,303,120 | B1 | * | 10/2001 | Danishefsky et al. .... 424/137.1 |
| 6,423,513 | B1 | * | 7/2002 | Fitzgerald .................. 435/71.3 |
| 6,426,075 | B1 | * | 7/2002 | Fitzgerald ................ 424/260.1 |
| 6,498,233 | B1 | * | 12/2002 | Wels et al. .................. 530/350 |
| 6,531,133 | B1 | | 3/2003 | Lorberboum-Galski et al. |
| 6,783,761 | B2 | * | 8/2004 | Grimes et al. ........... 424/185.1 |
| 6,881,718 | B1 | * | 4/2005 | FitzGerald et al. ............. 514/2 |
| 2002/0106370 | A1 | * | 8/2002 | Cardy et al. ............. 424/133.1 |
| 2004/0247617 | A1 | * | 12/2004 | Liao et al. ................ 424/192.1 |
| 2005/0079171 | A1 | * | 4/2005 | FitzGerald et al. ...... 424/133.1 |

FOREIGN PATENT DOCUMENTS

| | | | |
|---|---|---|---|
| EP | 0 439 954 A2 | | 12/1990 |
| EP | 439954 | * | 8/1991 |
| WO | 95/31483 | * | 11/1995 |
| WO | WO 95/31483 A1 | | 11/1995 |
| WO | WO 97/13529 | | 4/1997 |
| WO | WO 98/20135 | | 5/1998 |

OTHER PUBLICATIONS

Chaudhary, VK et al, Nature, vol. 335, Sep. 22, 1988, pp. 369-372.*
Cryz et al (1995)Vaccine, vol. 13, pp. 67-71.*
Moore, Chapter 2, p. 63-67, Synthetic Peptides Alesers Guide, WH Freeman & Co, N.Y.*
Swiss Prot Accession No. P11439, *Pseudomonas aerginosa* exotoxin A amino acid sequence entered in Oct. 1989.*
Cryz et al, 1995, Vaccine, vol. 13(1), pp. 67-71, Human immunodeficiency virus-1 principle neutralizing domain peptide-toxin A conjugate vaccine.*
Catasti, P et al, The Journal of Biological Chemistry, vol. 270(5), Feb. 3, 1995, 2224-2232, Local and Global Structural Properties of the HIV-MN V3 Loop.*
Donnelly, John J et al, PNAS, 1993, vol. 90, pp. 3530-3534, Apr. 1993.*
Brinkmann and Pastan, "Immunotoxins against cancer," *Biochimica et Biophysica Acta*, 1198:27-45 (1994).

Chaudhary, V.K. et al., "*Pseudomonas* exotoxin contains a specific sequence at the carboxyl terminus that is required for cytotoxicity," *Proc. Natl. Acad. Sci. USA*, 87:308-312 (1990).
Cryz, Jr., S.J. et al., "Human immunodeficiency virus-1 principal neutralizing domain peptide-toxin A conjugate vaccine," *Vaccine*, 13:67-71 (1995).
Cryz, Jr., S.J. et al., "Safety and Immunogenicity of a *Pseudomonas aeruginosa* O-Polysaccharide Toxin A Conjugate Vaccine in Humans," *J. Clin. Invest.*, 80:51-56 (1987).
Cryz, Jr., S.J. et al., "Safety and Immunogenicity of *Escherichia coli* O18 O-Specific Polysaccharide (O-PS)-Toxin and O-PS-Cholera Toxin Conjugate Vaccines in Humans," *J. Infectious Disease*, 163:1040-1045 (1990).
FitzGerald, D.J. et al., "Characterization of V3 Loop-Pseudomonas Exotoxin Chimeras," *J. of Biol. Chem.*, 273(16):9951-9958 (1998).
Lukac, M. et al., "Toxoid of *Pseudomonas aeruginosa* Exotoxin A Generated by Deletion of an Active-Site Residue," *Infection and Immunity*, 56(12):3095-3098 (1988).
Que, J.U. et al., "Effect of Carrier Selection on Immunogenicity of Protein Conjugate Vaccines against *Plasmodium falciparum* Circumsporozoites," *Infection and Immunity*, 56:2645-2649 (1988).
Reiter et al., "Engineering antibody Fv fragments for cancer detection and therapy: Disulfide-stabilized Fv -fragments," *Nature Biotechnology*, 14:1239-1245 (1996).
Backstrom, M. et al., "Insertion of a HIV-1-neutralizing epitope in a surface-exposed internal region of the cholera toxin B-subunit," *Gene*, 149:211-217 (1994).
Berman, P.W. et al., "Protection of chimpanzees from infection by HIV-1 after vaccination with recombinant glycoprotein gp120 but not gp160," *Nature*, 345:622-625 (1990).
Eaton, A.M. et al., "An Anti-gp41 Human Monoclonal Antibody That Enhances HIV-1 Infection in the Absence of Complement," *Aids Res. Hum. Retroviruses*, 10:13-18(1994).
Emini, E.A. et al., "Prevention of HIV-1 infection in chimpanzees by gp120 V3 domain-specific monoclonal antibody," *Nature*, 355:728-730 (1992).
Evans, D.J. et al., "An engineered poliovirus chimaera broadly reactive HIV-1 neutralizing anitboies," *Nature*, 339:385-388 (1989).
Fontenot, J.D. et al., "Human immunodeficiency virus (HIV) antigens: Structure and serology of multivalent human mucin MUC1-HIV V3 chimeric proteins," *Proc. Natl. Acad. Sci. USA*, 92:315-319.
Javaherian, K. et al., "Principal neutralizing domain of the human immunodeficiency virus type 1 envelope protein," *Proc. Natl. Acad. Sci. USA*, 86:6768-6772 (1989).
Kovacs, J.A. et al., "Induction of Humoral and Cell-mediated Anti-Human Immunodefieiency Virus (HIV Responses in HIV Sero-negative Volunteers by Immunization with Recombinant gp160," *J. Clin. Invest.*, 92:919-928 (1993).
Mitchell, W.M. et al., "Antibodies to the putative SIV infection-enhancing domain diminish beneficial effects of an SIV gp160 vaccine in rhesus macaques," *Aids*, 9:27-34 (1995).
Montefiori, D.C. et al., "Neutralizing and Infection-Enhancing Antibody Responses to Human Immunodeficiency Virus Type 1 in Long-Term Nonprogressors," *J. Infect. Dis.*, 173:60-67.
Rusche, J.R. et al., "Antibodies that inhibit fusion of human immunodeficiency virus-infected cells bind a 24-amino acid sequence of the viral envelope, gp120," *Proc. Natl. Acad. Sci. USA*, 85:3198-3202 (1988).
Steimer, K.S. et al., "Neutralization of Divergent HIV-1 Isolates by Conformation-Dependent Human Antibodies to Gp120," *Science*, 254:105-108 (1991).
Toth, F.D. et al., "Antibody-dependent enhancement of HIV-1 infection in human term syncytiotrophoblast cells cultured in vitro," *Clin. Exp. Immunol.*, 96:389-394.
Wang, C.Y. et al., "Long-Term High-Titer Neutralizing Activity Induced by Octameric Synthetic HIV-1 Antigen," *Science*, 254:285-288 (1991).
White-Scharf, M.E. et al., "Broadly Neutralizing Monoclonal Antibodies to the V3 Region of HIV-1 Can Be Elicited Peptide Immunization," *Virology*, 192:197-206 (1993).
U.S. Appl. No. 09/462,713, Fitzgerald.

Choe, et al. Cancer Res "B3(Fab)-PE38M: a recombinant immunotoxin in which a mutant form of *Pseudomonas* exotoxin is fused to the Fab fragment of monoclonal antibody B3" Jul. 1994 vol. 54, Issue 13 pp. 3460-3467.

Kreitman, et al. Bioconjug Chem "Properties of Chimeric Toxins with Two Recognition Domains: Interleukin 6 and transforming growth factor α at different locations in *Pseudomonas* Exotoxin" vol. 3, Issue 1 (1992) pp. 3-8.

Kuan, et al. J Biol Chem "*Pseudomonas* Exotoxin A Mutants. Replacement of Surface Exposed Residues in Domain II with Cysteine Residues that can be Modified with Polyethylene Glycol in a Site-Specific Manner" Mar. 1994 vol. 269, Issue 10 pp. 7610-7616.

Mansfield, et al. Bioconjug Chem "Characterization of RFB4-*Pseudomonas* Exotoxin A Immunotoxins Targeted to CD22 on B-Cell Malignancies" vol. 7, Issue 5, pp. 557-563 (1996).

Theuer, et al. Cancer Res "Immunotoxins made with a recombinant form of *Pseudomonas* exotoxin A that do not require proteolysis for activity" vol. 53, Issue 2, pp. 340-347 (Jan. 1993).

Kuan, et al. Proc. Natl. Acad. Sci USA "Improved antitumor activity of a recombinant anti-Lewis immunotoxin not requirieng proteolytic activation" vol. 93, pp. 974-978 (Feb. 1996).

U.S. Appl. No. 10/659,036, Fitzgerald et al.

Batra, J.K. et al.: "Single-chain immunotoxins directed at the human transferring receptor containing *Pseudomonas* exotoxin A or diphtheria toxin: anti-TFR(Fv)-PE40 and DT388-anti-TFR(Fv)" *Mol. Cell. Biol.*: vol. 11, No. 4; pp. 2200-2205 (Apr. 1991), Abstr. only.

Beraud, E. et al.: "Immunospecific suppression of encephalitogenic-activated T lymphocytes by chimeric cytotoxin IL-2-PE40" *Cell. Immunol.*; vol. 133, No. 2; pp. 379-389 (Apr. 1991), Abstr. only.

Choe, M. et al.: "B3(Fab)-PE38M: a recombinant immunotoxin in which a mutant form of *Pseudomonas* exototoxin is fused to the Fab fragment of monocional antibody B3" *Cancer Res.*; vol. 54, No. 13; pp. 3460-3467 (Jul. 1994), Abstr. only.

Debinski, W. and I. Pastan: "Recombinant F(ab') C242-*Pseudomonas* exotoxin, but not the whole antibody-based immunotoxin, causes regreassion of a colorectal tumor xenograft" *Clin. Cancer Res.*; vol. 1; pp. 1015-1022 (Sep. 1995).

Gawlak, S.L. et al.: "Basic fibroblast growth factor-*Pseudomonas* exotoxin chimeric proteins; comparison with acidic fibroblast growth factor-*Pseudomonas* exotoxin" *Bioconjug. Chem.*; vol. 4, No. 6; pp. 483-489, Abstr. only.

Gorse, G.J. et al.: "Salivari binding antibodies induced by human immunodeficiency virus type 1 recombinant gp120 vaccine" *Clinical and Diagnostic Laboratory Immunology*; vol. 3, No. 6; pp. 769-773 (1996).

Helmbrook, D.C. et al.: "Transforming growth factor alpha-*Pseudomonas* exotoxin fusion protein prolongs survival of nude mice bearing tumor xenografts" *Proc. Natl. Acad. Sci. USA*; vol. 87, No. 12; pp. 4697-4701 (Jun. 1990), Abstr. only.

Johansen, H. K. "Potential of preventing *Pseudomonas aeruginosa* lung infections in cystic fibrosis patients: experimental studies in animals" *APMIS Suppl.*; No. 63, vol. 104; pp. 5-42 (1996).

Johansen, H. K. et al.: "Clearance of *Pseudomonas aeruginosa* from normal rat lungs after immunization with somatic antigens or toxin A" *APMIS*; No. 102; pp. 545-553 (1994).

Kreitman, R.J. et al.: "Properties of chimeric toxins with two recognition domains: interleukin 6 and transforming growth factor alpha at different locations in *Pseudomonas* exotoxin" *Bioconjug. Chem.*; vol. 3, No. 1; pp. 63-68, Abstr. only.

Kreitman, RJ. and I. Pastan: "Purification and characterization of IL6-PE4E, a recombinant fusion of interleukin 6 with *Pseudomonas* exotoxin" *Bioconjug. Chem.*; vol. 4, No. 6; pp. 581-585, Abstr. only.

Kuan, C.T. and I. Pastan: "Improved antitumor activity of a recombinant anti-Lewis immunotoxin not requiring proteolytic activation" *Proc. Natl. Acad. Sci. USA*; vol. 93; pp. 974-978 (Feb. 1996).

Kuan, C.T. et al.: "Immunotoxins containing *Pseudomonas* exotoxin that target LeY damage human endothelial cells in an antibody-specific mode: relevance to vascular leak syndrome" *Clin. Cancer Res.*; vol. 1, No. 12; pp. 1589-1594 (Dec. 1995), Abstr. only.

Kuan, C.T. et al.: "*Pseudomonas* exotoxin A mutans. Replacement of surface exposed residues in domain II with cysteine residues that can be modified with polyethylene glycol in a site-specific manner" *J. Biol. Chem.*; vol. 269, No. 10; pp. 7610-7616 (Mar. 1994), Abstr. only.

Leger, O.J.P. et al.: "Humanization of a mouse antibody against alpha-4 integrin: a potential therapeutic for the treatment of multiple sclerosis" *Human Antibodies*; vol. 8; No. 1; pp. 3-16 (1997).

Mansfield, E. et al.: "Characterization of RFB4-*Pseudomonas* exotoxin A immunotoxins targeted to CD22 on B-cell malignancies" *Bioconjug. Chem.*; vol. 7, No. 5; pp. 557-563, Abstr. only.

Mickisch, G.H. et al.: "*Pseudomonas* exotoxin conjugated to monocional antibody MRK16 specifically kills multidrug resistant cells in cultured renal carcinomas and in MDR-transgenic mouse" *J. Urol.*; vol. 149, No. 1; pp. 174-178 (Jan. 1993), Abstr. only.

Pai, L.H. et al.: "Antitumor activity of a transforming growth factor alpha-*Pseudomonas* exotoxin fusion protein (TGF-alpha-PE40)" *Cancer Res.*; vol. 51, No. 11; pp. 2808-2812 (Jun. 1991), Abstr. only.

Pai, L.H. et al.: "Treatment of advanced solid tumors with immunotoxin LMB-1: an antibody linked to *Pseudomonas* exotoxin" *Nat. Med.*; vol. 2, No. 3; pp. 350-353 (Mar. 1996), Abstr. only.

Parr, E.L. and M. B. Parr: "Immunoglobulin G is the main protective antibody in mouse vaginal secretions after vaginal immunization with attenuated HSV-2." *J. Virol.*; pp. 8109-8115 (1997).

Puri, R.K. et al.: "A chimeric protein comprised of IL-4 and *Pseudomonas* exotoxin is cytotoxic for activated human lymphocytes" *J. Immunol.*; vol. 152, No. 7; pp. 3693-3700 (Apr. 1994), Abstr. only.

Reiter, Y et al.: "Cytotoxic and antitumor activity of a recombinant immunotoxin composed of disulfide-stabilized anti-Tac Fv fragment and truncated *Pseudomonas* exotoxin" *Int. J. Cancer*; vol. 58, No. 1; pp. 142-149 (Jul. 1994), Abstr. only.

Siegall, C.B. et al.: "In vivo activities of acidic fibroblast growth factor-*Pseudomonas* exotoxin fusion proteins" *Bioconjug. Chem.*; vol. 5, No. 1; pp. 77-83, Abstr. only.

Theuer, C. et al.: "Domain II of *Pseudomonas* exotoxin A arrests the transfer of translocating nascent chains into mammalian microsomes" *Biochemistry*; vol. 33, No. 19; pp. 5894-5900 (May 1994), Abstr. only.

Theuer, C.P. et al.: "Immunotoxins made with a recombinant form of *Pseudomonas* exotoxin A that do not require proteolysis for activity" *Cancer Res.*; vol. 53, No. 2; pp. 340-347 (Jan. 1993), Abstr. only.

Theuer, C.P. et al.: "The N-terminal region of the 37-kDa translocated fragment of *Pseudomonas* exotoxin A aborts translocation by promoting its own export after microsomal membrane insertion" *Proc. Acad. Natl. Sci. USA*; vol. 90, No. 16; pp. 7774-7778 (Aug. 1993), Abstr. only.

\* cited by examiner

1 A    Pseudomonas exotoxin    1 B    V3-loop toxin chimera

1 C

| Protein | Ib Loop Region Amino Acid Sequence | Molecular Mass |
|---|---|---|
| wild-type PE | -GAANADVVSLTCPVAAGECAGPAD- | 67,122 Da |
| ntPE-V3MN14 | -GAAN*LHC*GIHIGPGRAFYTTK*CMQ*GPAD- | 67,729 Da |
| ntPE-V3MN26 | -GAAN*LHC*NYNKRKRIHIGPGRAFYT TKNIIGTI*CMQ*GPAD- | 68,937 Da |
| ntPE-V3ThE26 | -GAAN*LHC*SNNTRTSITIGPGQVFYRT GDIIGDDI*CMQ*GPAD- | 68,700 Da |
| ntPE-FP16 | -GAAN*LQC*RLEEKKGNYVVTDHRL*CLQ*GPAD- | 67,862 Da |

Figure 1.

SDS-PAGE

1F12/MN

1B2/Th-E

Western blot Analysis

1F12/MN

1B2/Th-E

Antibody-mediated capture of proteins

3A

3B

3C

| Sample | % α-helix* | % ß-sheet | % ß-turns | % other |
|---|---|---|---|---|
| wild-type PE | 21 | 48 | 12 | 20 |
| ntPE-V3MN14 | 26 | 46 | 10 | 19 |
| ntPE-V3MN26 | 18 | 50 | 12 | 20 |

Serum IgG Response to Subcutaneous Injection of ntPE-MN26

- ■ ntPE-MN26 + Freund's Adjuvant (n=3)
- ▨ ntPE-MN26 + normal saline (n=3)
- □ ntPE + Freund's Adjuvant (n=2)

gp120-Specific IgG Relative to IF12 (µg/ml) vs. Days Post Initial Inoculation

SEQUENCE LISTING

```
<160> NUMBER OF SEQ ID NOS: 13

<210> SEQ ID NO 1
<211> LENGTH: 1839
<212> TYPE: DNA
<213> ORGANISM: Pseudomonas aeruginosa
<220> FEATURE:
<221> NAME/KEY: CDS
<222> LOCATION: (1)..(1839)
<223> OTHER INFORMATION: exotoxin A

<400> SEQUENCE: 1 gcc gaa gaa gct ttc gac ctc tgg aac gaa tgc gcc aaa gcc tgc gtg      48
Ala Glu Glu Ala Phe Asp Leu Trp Asn Glu Cys Ala Lys Ala Cys Val
  1               5                  10                  15
```

```
ctc gac ctc aag gac ggc gtg cgt tcc agc cgc atg agc gtc gac ccg      96
Leu Asp Leu Lys Asp Gly Val Arg Ser Ser Arg Met Ser Val Asp Pro
         20                  25                  30 gcc atc gcc gac acc aac ggc cag ggc gtg ctg cac tac tcc atg gtc     144
Ala Ile Ala Asp Thr Asn Gly Gln Gly Val Leu His Tyr Ser Met Val
             35                  40                  45 ctg gag ggc ggc aac gac gcg ctc aag ctg gcc atc gac aac gcc ctc     192
Leu Glu Gly Gly Asn Asp Ala Leu Lys Leu Ala Ile Asp Asn Ala Leu
 50                  55                  60 agc atc acc agc gac ggc ctg acc atc cgc ctc gaa ggc ggt gtc gag     240
Ser Ile Thr Ser Asp Gly Leu Thr Ile Arg Leu Glu Gly Gly Val Glu
 65                  70                  75                  80 ccg aac aag ccg gtg cgc tac agc tac acg cgc cag gcg cgc ggc agt     288
Pro Asn Lys Pro Val Arg Tyr Ser Tyr Thr Arg Gln Ala Arg Gly Ser
                 85                  90                  95 tgg tcg ctg aac tgg ctg gta ccg atc ggc cac gag aag ccc tcg aac     336
Trp Ser Leu Asn Trp Leu Val Pro Ile Gly His Glu Lys Pro Ser Asn
             100                 105                 110 atc aag gtg ttc atc cac gaa ctg aac gcc ggc aac cag ctc agc cac     384
Ile Lys Val Phe Ile His Glu Leu Asn Ala Gly Asn Gln Leu Ser His
         115                 120                 125 atg tcg ccg atc tac acc atc gag atg ggc gac gag ttg ctg gcg aag     432
Met Ser Pro Ile Tyr Thr Ile Glu Met Gly Asp Glu Leu Leu Ala Lys
 130                 135                 140 ctg gcg cgc gat gcc acc ttc ttc gtc agg gcg cac gag agc aac gag     480
Leu Ala Arg Asp Ala Thr Phe Phe Val Arg Ala His Glu Ser Asn Glu
145                 150                 155                 160 atg cag ccg acg ctc gcc atc agc cat gcc ggg gtc agc gtg gtc atg     528
Met Gln Pro Thr Leu Ala Ile Ser His Ala Gly Val Ser Val Val Met
                 165                 170                 175 gcc cag acc cag ccg cgc cgg gaa aag cgc tgg agc gaa tgg gcc agc     576
Ala Gln Thr Gln Pro Arg Arg Glu Lys Arg Trp Ser Glu Trp Ala Ser
             180                 185                 190 ggc aag gtg ttg tgc ctg ctc gac ccg ctg gac ggg gtc tac aac tac     624
Gly Lys Val Leu Cys Leu Leu Asp Pro Leu Asp Gly Val Tyr Asn Tyr
         195                 200                 205 ctc gcc cag caa cgc tgc aac ctc gac gat acc tgg gaa ggc aag atc     672
Leu Ala Gln Gln Arg Cys Asn Leu Asp Asp Thr Trp Glu Gly Lys Ile
 210                 215                 220 tac cgg gtg ctc gcc ggc aac ccg gcg aag cat gac ctg gac atc aaa     720
Tyr Arg Val Leu Ala Gly Asn Pro Ala Lys His Asp Leu Asp Ile Lys
225                 230                 235                 240 ccc acg gtc atc agt cat cgc ctg cac ttt ccc gag ggc ggc agc ctg     768
Pro Thr Val Ile Ser His Arg Leu His Phe Pro Glu Gly Gly Ser Leu
                 245                 250                 255 gcc gcg ctg acc gcg cac cag gct tgc cac ctg ccg ctg gag act ttc     816
Ala Ala Leu Thr Ala His Gln Ala Cys His Leu Pro Leu Glu Thr Phe
             260                 265                 270 acc cgt cat cgc cag ccg cgc ggc tgg gaa caa ctg gag cag tgc ggc     864
Thr Arg His Arg Gln Pro Arg Gly Trp Glu Gln Leu Glu Gln Cys Gly
         275                 280                 285 tat ccg gtg cag cgg ctg gtc gcc ctc tac ctg gcg gcg cgg ctg tcg     912
Tyr Pro Val Gln Arg Leu Val Ala Leu Tyr Leu Ala Ala Arg Leu Ser
 290                 295                 300 tgg aac cag gtc gac cag gtg atc cgc aac gcc ctg gcc agc ccc ggc     960
Trp Asn Gln Val Asp Gln Val Ile Arg Asn Ala Leu Ala Ser Pro Gly
305                 310                 315                 320 agc ggc ggc gac ctg ggc gaa gcg atc cgc gag cag ccg gag cag gcc    1008
Ser Gly Gly Asp Leu Gly Glu Ala Ile Arg Glu Gln Pro Glu Gln Ala
```

```
                         325                 330                 335
cgt ctg gcc ctg acc ctg gcc gcc gcc gag agc gag cgc ttc gtc cgg    1056
Arg Leu Ala Leu Thr Leu Ala Ala Ala Glu Ser Glu Arg Phe Val Arg
                340                 345                 350 cag ggc acc ggc aac gac gag gcc ggc gcg gcc aac gcc gac gtg gtg    1104
Gln Gly Thr Gly Asn Asp Glu Ala Gly Ala Ala Asn Ala Asp Val Val
            355                 360                 365 agc ctg acc tgc ccg gtc gcc gcc ggt gaa tgc gcg ggc ccg gcg gac    1152
Ser Leu Thr Cys Pro Val Ala Ala Gly Glu Cys Ala Gly Pro Ala Asp
    370                 375                 380 agc ggc gac gcc ctg ctg gag cgc aac tat ccc act ggc gcg gag ttc    1200
Ser Gly Asp Ala Leu Leu Glu Arg Asn Tyr Pro Thr Gly Ala Glu Phe
385                 390                 395                 400 ctc ggc gac ggc ggc gac gtc agc ttc agc acc cgc ggc acg cag aac    1248
Leu Gly Asp Gly Gly Asp Val Ser Phe Ser Thr Arg Gly Thr Gln Asn
                405                 410                 415 tgg acg gtg gag cgg ctg ctc cag gcg cac cgc caa ctg gag gag cgc    1296
Trp Thr Val Glu Arg Leu Leu Gln Ala His Arg Gln Leu Glu Glu Arg
            420                 425                 430 ggc tat gtg ttc gtc ggc tac cac ggc acc ttc ctc gaa gcg gcg caa    1344
Gly Tyr Val Phe Val Gly Tyr His Gly Thr Phe Leu Glu Ala Ala Gln
    435                 440                 445 agc atc gtc ttc ggc ggg gtg cgc gcg cgc agc cag gac ctc gac gcg    1392
Ser Ile Val Phe Gly Gly Val Arg Ala Arg Ser Gln Asp Leu Asp Ala
450                 455                 460 atc tgg cgc ggt ttc tat atc gcc ggc gat ccg gcg ctg gcc tac ggc    1440
Ile Trp Arg Gly Phe Tyr Ile Ala Gly Asp Pro Ala Leu Ala Tyr Gly
465                 470                 475                 480 tac gcc cag gac cag gaa ccc gac gca cgc ggc cgg atc cgc aac ggt    1488
Tyr Ala Gln Asp Gln Glu Pro Asp Ala Arg Gly Arg Ile Arg Asn Gly
                485                 490                 495 gcc ctg ctg cgg gtc tat gtg ccg cgc tcg agc ctg ccg ggc ttc tac    1536
Ala Leu Leu Arg Val Tyr Val Pro Arg Ser Ser Leu Pro Gly Phe Tyr
            500                 505                 510 cgc acc agc ctg acc ctg gcc gcg ccg gag gcg gcg ggc gag gtc gaa    1584
Arg Thr Ser Leu Thr Leu Ala Ala Pro Glu Ala Ala Gly Glu Val Glu
    515                 520                 525 cgg ctg atc ggc cat ccg ctg ccg ctg cgc ctg gac gcc atc acc ggc    1632
Arg Leu Ile Gly His Pro Leu Pro Leu Arg Leu Asp Ala Ile Thr Gly
530                 535                 540 ccc gag gag gaa ggc ggg cgc ctg gag acc att ctc ggc tgg ccg ctg    1680
Pro Glu Glu Glu Gly Gly Arg Leu Glu Thr Ile Leu Gly Trp Pro Leu
545                 550                 555                 560 gcc gag cgc acc gtg gtg att ccc tcg gcg atc ccc acc gac ccg cgc    1728
Ala Glu Arg Thr Val Val Ile Pro Ser Ala Ile Pro Thr Asp Pro Arg
                565                 570                 575 aac gtc ggc ggc gac ctc gac ccg tcc agc atc ccc gac aag gaa cag    1776
Asn Val Gly Gly Asp Leu Asp Pro Ser Ser Ile Pro Asp Lys Glu Gln
            580                 585                 590 gcg atc agc gcc ctg ccg gac tac gcc agc cag ccc ggc aaa ccg ccg    1824
Ala Ile Ser Ala Leu Pro Asp Tyr Ala Ser Gln Pro Gly Lys Pro Pro
    595                 600                 605 cgc gag gac ctg aag                                                1839
Arg Glu Asp Leu Lys
    610

<210> SEQ ID NO 2
<211> LENGTH: 613
<212> TYPE: PRT
<213> ORGANISM: Pseudomonas aeruginosa
```

-continued

<400> SEQUENCE: 2

```
Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
```

-continued

```
                    405                 410                 415
Trp Thr Val Glu Arg Leu Leu Gln Ala His Arg Gln Leu Glu Glu Arg
                420                 425                 430
Gly Tyr Val Phe Val Gly Tyr His Gly Thr Phe Leu Glu Ala Ala Gln
                435                 440                 445
Ser Ile Val Phe Gly Gly Val Arg Ala Arg Ser Gln Asp Leu Asp Ala
            450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Ser Ser Leu Pro Gly Phe Tyr
                500                 505                 510
Arg Thr Ser Leu Thr Leu Ala Ala Pro Glu Ala Ala Gly Glu Val Glu
                515                 520                 525
Arg Leu Ile Gly His Pro Leu Pro Leu Arg Leu Asp Ala Ile Thr Gly
                530                 535                 540
Pro Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                565                 570                 575
Asn Val Gly Gly Asp Leu Asp Pro Ser Ser Ile Pro Asp Lys Glu Gln
                580                 585                 590
Ala Ile Ser Ala Leu Pro Asp Tyr Ala Ser Gln Pro Gly Lys Pro Pro
                595                 600                 605
Arg Glu Asp Leu Lys
    610

<210> SEQ ID NO 3
<211> LENGTH: 35
<212> TYPE: PRT
<213> ORGANISM: Human immunodeficiency virus type 1
<220> FEATURE:
<221> NAME/KEY: PEPTIDE
<222> LOCATION: (1)..(35)
<223> OTHER INFORMATION: V3 loop of MN strain of HIV-1

<400> SEQUENCE: 3

Cys Thr Arg Pro Asn Tyr Asn Lys Arg Lys Arg Ile His Ile Gly Pro
  1               5                  10                  15
Gly Arg Ala Phe Tyr Thr Thr Lys Asn Ile Ile Gly Thr Ile Arg Gln
                 20                  25                  30
Ala His Cys
        35

<210> SEQ ID NO 4
<211> LENGTH: 35
<212> TYPE: PRT
<213> ORGANISM: Human immunodeficiency virus type 1
<220> FEATURE:
<221> NAME/KEY: PEPTIDE
<222> LOCATION: (1)..(35)
<223> OTHER INFORMATION: V3 loop of Thai-E strain of HIV-1

<400> SEQUENCE: 4

Cys Thr Arg Pro Ser Asn Asn Thr Arg Thr Ser Ile Thr Ile Gly Pro
  1               5                  10                  15
Gly Gln Val Phe Tyr Arg Thr Gly Asp Ile Ile Gly Asp Ile Arg Lys
                 20                  25                  30
```

Ala Tyr Cys
    35

<210> SEQ ID NO 5
<211> LENGTH: 90
<212> TYPE: DNA
<213> ORGANISM: Artificial Sequence
<220> FEATURE:
<223> OTHER INFORMATION: Description of Artificial Sequence:coding
      strand of duplex containing novel PstI site

<400> SEQUENCE: 5
tggccctgac cctggccgcc gccgagagcg agcgcttcgt ccggcagggc accggcaacg    60
acgaggccgg cgcggcaaac ctgcagggcc    90

<210> SEQ ID NO 6
<211> LENGTH: 24
<212> TYPE: PRT
<213> ORGANISM: Pseudomonas aeruginosa
<220> FEATURE:
<221> NAME/KEY: PEPTIDE
<222> LOCATION: (1)..(24)
<223> OTHER INFORMATION: Ib loop region of wild-type Pseudomonas
      exotoxin A

<400> SEQUENCE: 6

Gly Ala Ala Asn Ala Asp Val Val Ser Leu Thr Cys Pro Val Ala Ala
 1               5                  10                  15

Gly Glu Cys Ala Gly Pro Ala Asp
            20

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence:Ib loop
      region of ntPE-V34MN14 protein

<400> SEQUENCE: 7

Gly Ala Ala Asn Leu His Cys Gly Ile His Ile Gly Pro Gly Arg Ala
 1               5                  10                  15

Phe Tyr Thr Thr Lys Cys Met Gln Gly Pro Ala Asp
            20                  25

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence:Ib loop
      region of ntPE-V3MN26 protein

<400> SEQUENCE: 8

Gly Ala Ala Asn Leu His Cys Asn Tyr Asn Lys Arg Lys Arg Ile His
 1               5                  10                  15

Ile Gly Pro Gly Arg Ala Phe Tyr Thr Thr Lys Asn Ile Ile Gly Thr
            20                  25                  30

Ile Cys Met Gln Gly Pro Ala Asp
        35                  40

<210> SEQ ID NO 9
<211> LENGTH: 41
<212> TYPE: PRT

<210> SEQ ID NO 9
<211> LENGTH: (not shown)
<212> TYPE: PRT
<213> ORGANISM: Artificial Sequence
<220> FEATURE:
<223> OTHER INFORMATION: Description of Artificial Sequence:Ib loop
      region of ntPE-V3Th-E26 protein

<400>

PSEUDOMONAS EXOTOXIN A-LIKE CHIMERIC IMMUNOGENS

CROSS-REFERENCE TO RELATED APPLICATION

This application claims the benefit of the filing date of co-pending application 60/052,375, filed Jul. 11, 1997, the content of which is incorporated herein by reference in its entirety.

BACKGROUND OF THE INVENTION

This invention is directed to the fields of chimeric proteins and immunology.

Immunization against infectious disease has been one of the great achievements of modern medicine. Vaccines can be useful only if the vaccine, itself, is not significantly pathogenic. Many vaccines are produced by inactivating the pathogen. For example, hepatitis vaccines can be made by heating the virus and treating it with formaldehyde. Other vaccines, for example certain polio vaccines, are produced by attenuating a live pathogen. However, there is concern about producing attenuated vaccines for certain infectious agents whose pathology is not fully understood, such as HIV.

Molecular biology has enabled the production of subunit vaccines; vaccines in which the immunogen is a fragment or subunit of a parent protein or complex. Envelope proteins of HIV-1, such as gp120, are being evaluated as subunit vaccines. Several studies have suggested that antibodies to the V3 loop region of gp120 provide protection through virus neutralization. (Emini, E. A., et al., 1992, *Nature* 355, 728-30; Javaherian, K., et al., 1989, *Proc Natl Acad Sci USA* 86, 6768-72; Steimer, K. S., et. al., 1991, *Science* 254, 105-8; Wang, C. Y., et al., 1991, *Science* 254, 285-8.)

However, subunit vaccines may not be complex enough to generate an appropriate immune response. Also, when the pathogen is highly mutable, as is HIV, subunit vaccines that elicit strain-specific immunity may not be effective in providing global protection. Furthermore, the injection of inactive virus or even the envelope protein itself has the potential to produce a mixture of neutralizing and so-called "enhancing" antibodies. (Toth, F. D., et al., 1994, *Clin Exp Immunol* 96, 389-94; Eaton, A. M., et al., 1994, *Aids Res Hum Retroviruses* 10, 13-8; Mitchell, W. M., et al., 1995, *Aids* 9, 27-34; Montefiori, D. C., et al., 1996, *J Infect Dis* 173, 60-7.)

The immunogenicity of subunit vaccines is sometimes increased by coupling the subunit to a carrier protein to create a conjugate vaccine. One such carrier protein is *Pseudomonas* exotoxin A ("PE"). Investigators covalently linked a non-immunogenic O-polysaccharide derived from lipopolysaccharide ("LPS") to PE. The resulting conjugate vaccine elicited an immune response against both LPS and PE. (S. J. Cryz, Jr. et al. (1987) *J. Clin. Invest.*, 80:51-56 and S. J. Cryz, Jr. et al. (1990) *J. Infectious Diseases,* 163:1040-1045.) In another study, investigators were able to evoke an immune response against a *Plasmodium falciparum* antigen by coupling it through a spacer to PE. (J. U. Que et al. (1988) *Infection and Immunity,* 56:2645-49.) In a third study, investigators detoxified PE and chemically cross-linked it with principle neutralizing domain ("PND") peptides of HIV-1. The conjugate vaccine elicited the production of antibodies that recognized PND peptide and neutralized the homologous strain, HIV-1$_{MN}$. (S. J. Cryz, Jr et al. (1995) *Vaccine,* 13:66-71.)

Chimeric proteins containing components of HIV-1 have been constructed and their immunogenic properties evaluated. These include: a poliovirus antigen containing an epitope of the gp41 transmembrane glycoprotein from HIV-1 (Evans, D. J., et al., 1989, *Nature* 339, 385-8), a mucin protein containing multiple copies of the V3 loop (Fontenot, J. D., et al., 1995, *Proc Natl Acad Sci USA,* 92, 315-9) a genetically modified cholera B chain with V3 loop sequences (Backstrom, M., et. al., 1994, *Gene* 149, 211-7) and a chemically detoxified PE-V3 loop peptide conjugate (Cryz, S., Jr., et al., 1995, *Vaccine* 13, 67-71).

The third variable (V3) loop of the envelope protein, gp120, contains the principal neutralizing domain of HIV-1. (Emini, E. A., et al., 1992, *Nature* 355, 728-30; Javaherian, K., et al., 1989, *Proc Natl Acad Sci USA* 86, 6768-72; Rusche, J. R., et al., [published errata appear in *Proc Natl Acad Sci USA* 22, 8697 1988, and *Proc Natl Acad Sci USA* 5, 1667 1989,]; *Proc Natl Acad Sci USA* 85, 3198-202 1988.) Although V3 loops vary considerably amongst the various HIV-1 strains (Berman, P. W., et al., 1990, *Nature* 345, 622-5) specific antibodies to this region have been shown to neutralize infectivity of the virus and to prevent viral cell fusion in vitro (Kovacs, J. A., et al. 1993, *J. Clin Invest* 92, 919-28). Further, systemic immunization with a recombinant form of gp120 appears sufficient to protect chimpanzees from infection by HIV-1 systemic challenge. Whitescarf, M. E., et al., 1993, *Virology* 192, 197-206.

HIV frequently gains entry to the body at mucosal surfaces. However, presently available HIV immunogens are not known to elicit a secretory immune response, which would inhibit viral access through the mucosa.

The development of a stable vaccine that could elicit both humoral and cellular responses, including mucosal immunity, and be flexible enough to incorporate sequences from many strains of an infectious agent, such as HIV-1, would be desirable.

SUMMARY OF THE INVENTION

*Pseudomonas* exotoxin A-like ("PE-like") chimeric immunogens in which a non-native epitope is inserted into the Ib domain are useful to elicit humoral, cell-mediated and secretory immune responses against the non-native epitope. In particular, the non-native epitope can be the V3 loop of the gp120 protein of HIV. Such chimeras are useful in vaccines against HIV infection.

PE chimeric immunogens offer several advantages. First, they can be made by wholly recombinant means. This eliminates the need to attach the epitope to PE by chemical cross-linking and to chemically inactivate the exotoxin. Recombinant technology also allows one to make a chimeric "cassette" having an insertion site for the non-native epitope of choice at the Ib domain location. This allows one to quickly insert existing variants of an epitope, or new variants of rapidly evolving epitopes. This enables production of vaccines that include a cocktail of different immunogens.

Second, *Pseudomonas* exotoxin can be engineered to alter the function of its domains, thereby providing a variety of activities. For example, by replacing the native cell binding domain of *Pseudomonas* exotoxin A (domain Ia) with a ligand for a particular cell receptor, one can target the chimera to bind to the particular cell type.

Third, because the Ib domain includes a cysteine-cysteine loop, epitopes that are so constrained in nature can be presented in near-native conformation. This assists in provoking an immune response against the native antigen. For example, a turn-turn-helix motif is evident with circular (constrained by a disulfide bond) but not linear peptides. (Ogata, M., et. al., 1990, *Biol Chem* 265, 20678-85.) Also, circular peptides are recognized more readily by anti-V3 loop monoclonal antibodies than linear ones. (Catasti, P., et. al., 1995, *J Biol Chem* 270, 2224-32.)

Fourth, the chimeras of this invention can be used to elicit a humoral, a cell-mediated or a secretory immune response. *Pseudomonas* exotoxin has been reported to act as a "superantigen," binding directly to MHC Class II molecules without prior processing in the antigen presenting cell. P. K. Legaard et al. (1991) *Cellular Immunology* 135:372-382. This promotes an MHC Class II-mediated immune response against cells bearing proteins containing the non-native epitope. Also, upon binding to a cell surface receptor, chimeric *Pseudomonas* exotoxins translocate into the cytosol. This makes possible an MHC Class I-dependent immune response against cells bearing the non-native epitope on their surface. This aspect is particularly advantageous because normally the immune system mounts an MHC Class I-dependent immune response only against proteins made by the cell. Also, by directing the chimera to a mucosal surface, one can elicit a secretory immune response involving IgA.

In one aspect, this invention provides a non-toxic *Pseudomonas* exotoxin A-like ("PE-like") chimeric immunogen comprising: (1) a cell recognition domain of between 10 and 1500 amino acids that binds to a cell surface receptor; (2) a translocation domain comprising an amino acid sequence substantially identical to a sequence of PE domain II sufficient to effect translocation to a cell cytosol; (3) a non-native epitope domain comprising an amino acid sequence of between 5 and 1500 amino acids that comprises a non-native epitope; and, optionally, (4) an amino acid sequence encoding an endoplasmic reticulum ("ER") retention domain that comprises an ER retention sequence. In one embodiment, the chimeric immunogen comprises the amino acid sequence of a non-toxic PE wherein domain Ib further comprises the non-native epitope between two cysteine residues of domain Ib.

In certain embodiments the cell recognition domain binds to α2-macroglobulin receptor ("α2-MR"), epidermal growth factor ("EGF") receptor, IL-2 receptor, IL-6 receptor, human transferrin receptor or gp120. In another embodiment, the cell recognition domain comprises amino acid sequences of a growth factor. In another embodiment, the translocation domain comprises amino acids 280 to 364 of domain II of PE. In another embodiment, the non-native epitope domain comprises a cysteine-cysteine loop that comprises the non-native epitope. In another embodiment, the non-native epitope domain comprises an amino acid sequence selected from the V3 loop of HIV-1. In another embodiment, the ER retention domain is domain III of PE comprising a mutation that eliminates ADP ribosylation activity, such as ΔE553. The ER retention domain can comprise the ER retention sequence REDLK (SEQ ID NO: 11), REDL (SEQ ID NO: 12) or KDEL (SEQ ID NO: 13). In another embodiment the non-native epitope is an epitope from a pathogen (e.g., an epitope from a virus, bacterium or parasitic protozoa) or from a cancer antigen.

In another embodiment the cell recognition domain is domain Ia of PE, the translocation domain is domain II of PE, the non-native epitope domain comprises an amino acid sequence encoding a non-native epitope inserted between two cysteine residues of domain Ib of PE, and the ER retention domain is domain III of PE and comprises a mutation that eliminates ADP ribosylation activity.

In another aspect, this invention provides a recombinant polynucleotide comprising a nucleotide sequence encoding a non-toxic *Pseudomonas* exotoxin A-like chimeric immunogen of this invention. In one embodiment, the recombinant polynucleotide is an expression vector further comprising an expression control sequence operatively linked to the nucleotide sequence.

In another aspect, this invention provides a recombinant *Pseudomonas* exotoxin A-like chimeric immunogen cloning platform comprising a nucleotide sequence encoding: (1) a cell recognition domain of between 10 and 1500 amino acids that binds to a cell surface receptor; (2) a translocation domain comprising an amino acid sequence substantially identical to a sequence of PE domain II sufficient to effect translocation to a cell cytosol; (3) an amino acid sequence encoding an endoplasmic reticulum ("ER") retention domain that comprises an ER retention sequence and, optionally, (4) a splicing site between the sequence encoding the translocation domain and the sequence encoding the ER retention domain. In one embodiment the recombinant polynucleotide is an expression vector further comprising an expression control sequence operatively linked to the nucleotide sequence.

In another aspect this invention provides a method of producing antibodies against a non-native epitope naturally within a cysteine-cysteine loop. The method comprises the step of inoculating an animal with a non-toxic *Pseudomonas* exotoxin A-like chimeric immunogen of this invention wherein the non-native epitope domain comprises a cysteine-cysteine loop that comprises the non-native epitope.

In another aspect this invention provides a vaccine comprising at least one *Pseudomonas* exotoxin A-like chimeric immunogen comprising a cell recognition domain, a translocation domain, a non-native epitope domain comprising a non-native epitope and an endoplasmic reticulum ("ER") retention domain comprising an ER retention sequence. In one embodiment the vaccine comprises a plurality of PE-like chimeric immunogens, each immunogen having a different non-native epitope. In another embodiment the different non-native epitopes are epitopes of different strains of the same pathogen.

In another aspect this invention provides a method of eliciting an immune response against a non-native epitope in a subject. The method comprises the step of administering to the subject a vaccine comprising at least one *Pseudomonas* exotoxin A-like chimeric immunogen of this invention. In one embodiment, the non-native epitope comprises a binding motif for an MHC Class II molecule of the subject and the immune response elicited is an MHC Class-II dependent cell-mediated immune response. In another embodiment the non-native epitope comprises a binding motif for an MHC Class I molecule of the subject and the immune response elicited is an MHC Class-I dependent cell-mediated immune response.

In another aspect this invention provides a polynucleotide vaccine comprising at least one recombinant polynucleotide comprising a nucleotide sequence encoding a non-toxic *Pseudomonas* exotoxin A-like chimeric immunogen of this invention.

In another aspect, this invention provides a method of eliciting an immune response against a non-native epitope in a subject. The method comprises the step of administering to the subject a polynucleotide vaccine comprising at least one recombinant polynucleotide comprising a nucleotide sequence encoding a non-toxic *Pseudomonas* exotoxin A-like chimeric immunogen of this invention. In one embodiment, the recombinant polynucleotide is an expression vector comprising an expression control sequence operatively linked to the nucleotide sequence.

In another aspect this invention provides a method of eliciting an immune response against a non-native epitope in a subject, the method comprising the steps of transfecting cells with a recombinant polynucleotide comprising a nucleotide sequence encoding a non-toxic *Pseudomonas* exotoxin A-like chimeric immunogen of this invention, and administering the cells to the subject.

In another aspect, this invention provides methods of eliciting an IgA-mediated secretory immune response. The methods involve administering to a mucosal membrane a non-toxic *Pseudomonas* chimeric immunogen of this invention, wherein the cell recognition domain binds to a receptor on a mucosal membrane. The cell recognition domain can bind to α2-MR (e.g., the native cell recognition domain of PE), or to the EGF receptor. The mucosal surface can be mouth, nose, lung, gut, vagina, colon or rectum.

In another aspect, this invention provides a composition comprising secretory IgA antibodies that specifically recognize an epitope of a pathogen that enters the body through a mucosal surface, e.g., an epitope of HIV-1.

BRIEF DESCRIPTION OF THE DRAWINGS

FIGS. 1A-1C. (A and B) A schematic depiction of PE and a PE-V3 loop chimera showing the relative location of the Ib and V3 loops between domains II and III. Approximate location of the single amino acid deletion (ΔE553) to ablate PE toxicity is also shown. (C) Amino acid sequences, represented with single letter code, which replaced the Ib loop of wild-type PE with a V3 loop sequence of gp120 (bold type) from either the MN or Thai-E (TE) strains of HIV-1 contained two cysteine residues designed to result in a loop conformation following disulfide bond formation. The insertion of a unique PstI restriction site, used for introduction of V3 loop sequences, resulted in several modifications of the wild-type PE amino add sequence adjacent to the Ib loop (italics). An irrelevant control peptide insert was prepared as a control and is designated ntPE-fp16. Calculated molecular masses are shown for full-length expressed proteins. Wild-type PE—SEQ ID NO:6; ntPE-V3MN14—SEQ ID NO:7; ntPE-V3MN26—SEQ ID NO:8; ntPE-V3Th-E26—SEQ ID NO:9; ntPE-fp16—SEQ ID NO: 10.

FIG. 12 shows serum levels of IgG following mucosal or systemic inoculation with ntPE-V3MN26. MN-gp120 specific IgG antibodies were measured in serum samples by ELISA and standardized against a mouse monoclonal antibody which specifically recognizes the V3 loop of MNgp120.

FIG. 13 shows serum levels of IgG following subcutaneous injection of ntPE-V3MN26. The immune response produced from injection of ntPE-V3MN26 (hatched bars) was compared to that induced when co-injected with a regimen of Freund's complete and incomplete adjuvant (solid bars). Non-toxic PE not containing the 26 amino acids from the V3 loop of MNgp120 was injected with the same adjuvant regimen as a control. MN-gp120 specific IgG antibodies were measured in serum samples by ELISA and standardized against a mou product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Figure 2A:
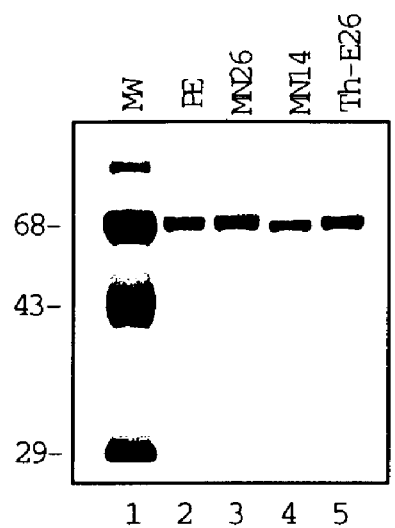
FIGS. 2A-2C. Characterization of ntPE-V3 loop chimeras after separation by SDS-PAGE. (A) Coomasie blue staining of purified ntPE-V3 loop chimeras following separation by SDS-PAGE. Approximately 1 μg of protein was loaded on each lane. (B) Western blot analysis of ntPE-V3 loop chimeras. After transfer to Immobilon P membranes, proteins were probed with monoclonal antibodies raised against intact gp120/MN (1F12) or gp120/Thai-E (1B2). An irrelevant sequence of 16 amino adds was inserted into the Ib loop region of ntPE (ntPE-fp16) and was used here as a negative control. (C) Immunocapture studies, using either 1F12 or 1B2 immobilized on protein G sepharose, were used to characterize the exposure of V3 loop sequences on the surface of the various chimeric proteins. Proteins were visualized by staining gels with Coomasie blue. Gp120 and ntPE-fp16 were used as positive and negative controls respectively. The capture of PE-V3 loop proteins is indicated with a single arrowhead and of gp120 by a double arrowhead. The left panel shows the presence of the antibody heavy chain (hc) only since the light chain (1c) was run off the gel. The right panel shows both chains.
Figure 2B:
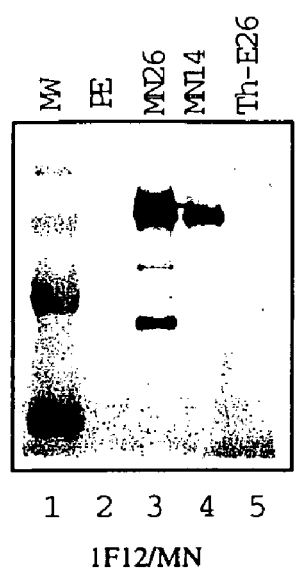
Figure 2B:
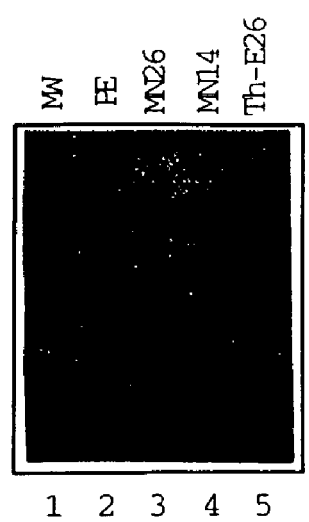
Figure 2C:
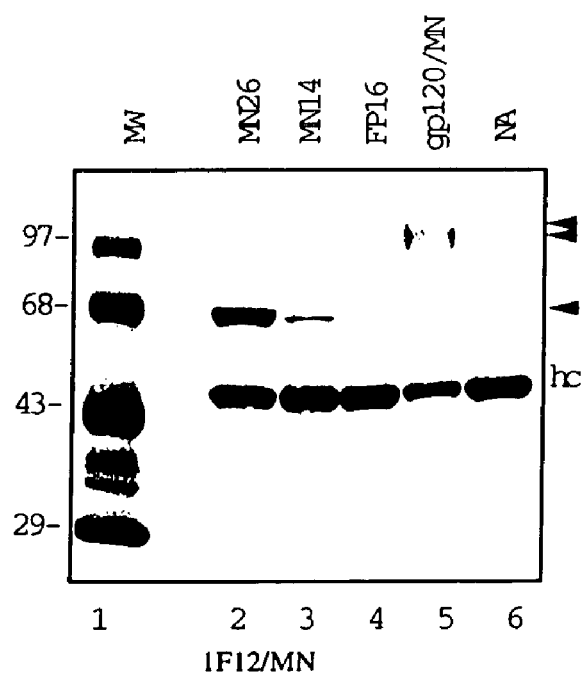
Figure 2C:
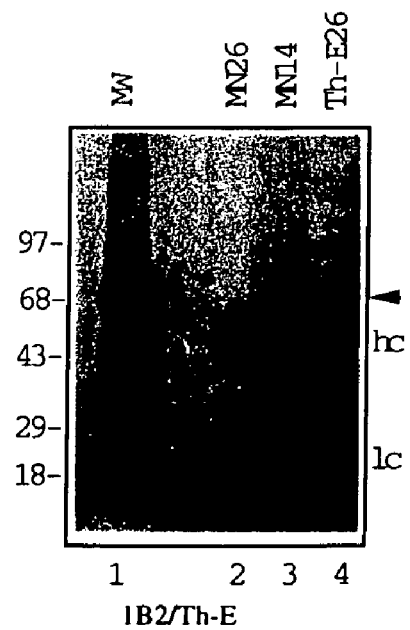

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

A first sequence is an "antisense sequence" with respect to a second sequence if a polynucleotide whose sequence is the first sequence specifically hybridizes with a polynucleotide whose sequence is the second sequence.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, 80%, 90%, 95% or 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described herein.

A "ligand" is a compound that specifically binds to a target molecule.

A "receptor" is compound that specifically binds to a ligand.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies and humanized antibodies. "Fc" portion of an antibody refers to that portion of an immunoglobulin heavy chain that comprises one or more heavy chain constant region domains, $CH_1$, $CH_2$ and $CH_1$, but does not include the heavy chain variable region.

A ligand or a receptor (e.g., an antibody) "specifically binds to" or "is specifically immunoreactive with" a compound analyte when the ligand or receptor functions in a binding reaction which is determinative of the presence of the analyte in a sample of heterogeneous compounds. Thus, under designated assay (e.g., immunoassay) conditions, the ligand or receptor binds preferentially to a particular analyte and does not bind in a significant amount to other compounds present in the sample. For example, a polynucleotide specifically binds under hybridization conditions to an analyte polynucleotide comprising a complementary sequence; an antibody specifically binds under immunoassay conditions to an antigen analyte bearing an epitope against which the antibody was raised; and an adsorbent specifically binds to an analyte under proper elution conditions.

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Vaccine" refers to an agent or composition containing an agent effective to confer a therapeutic degree of immunity on an organism while causing only very low levels of morbidity or mortality. Methods of making vaccines are, of course, useful in the study of the immune system and in preventing and treating animal or human disease.

An "immunogenic amount" is an amount effective to elicit an immune response in a subject.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, *Bio/Technology* (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences,* 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

A "subject" of diagnosis or treatment is a human or non-human animal, including a mammal or a primate.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Prognostic" means predicting the probable development (e.g., severity) of a pathologic condition.

"Plurality" means at least two.

"*Pseudomonas* exotoxin A" or "PE" is secreted by Ps aeruginosa as a 67 kD protein composed of three prominent globular domains (Ia, II, and III) and one small subdomain (Ib) connecting domains II and III. (A. S. Allured et. al. (1986) *Proc. Natl. Acad. Sci.* 83:1320-1324.) Domain Ia of PE mediates cell binding. In nature, domain Ia binds to the low density lipoprotein receptor-related protein ("LRP"), also known as the α2-macroglobulin receptor ("β2-MR"). (M. Z. Kounnas et al. (1992) *J. Biol. Chem.* 267:12420-23.) It spans amino acids 1-252. Domain II mediates translocation to the cytosol. It spans amino acids 253-364. Domain Ib has no known function. It spans amino acids 365-399. Domain III is responsible for cytotoxicity and includes an endoplasmic reticulum retention sequence. It mediates ADP ribosylation of elongation factor 2, which inactivates protein synthesis. It spans amino acids 400-613. PE is "non-toxic" if it lacks EF2 ADP ribosylation activity. Deleting amino acid E553 ("ΔE553") from domain III detoxifies the molecule. PE having the mutation ΔE553 is referred to herein as "PE ΔE553." Genetically modified forms of PE are described in, e.g., Pastan et al., U.S. Pat. No. 5,602,095; Pastan et al., U.S. Pat. No. 5,512,658 and Pastan et al., U.S. Pat. No. 5,458,878. Allelic forms of PE are included in this definition. See, e.g., M. L. Vasil et al., (1986) *Infect. Immunol.* 52:538-48. "Cysteine-cysteine loop" refers to a peptide moiety in a polypeptide that is defined by an amino acid sequence bordered by two disulfide-bonded cysteine residues.

"Non-native epitope" refers to an epitope encoded by an amino acid sequence that does not naturally occur in the Ib domain of *Pseudomonas* exotoxin A.

II. *Pseudomonas* Exotoxin A-Like Chimeric Immunogens

A. Basic Structure

The *Pseudomonas* exotoxin A-like ("PE-like") chimeric immunogens of this invention are polypeptides having structural domains organized, except as provided herein, in the same sequence as the four structural domains of PE (i.e., Ia, II, Ib and III), and having certain functions (e.g., cell recognition, cytosolic translocation and endoplasmic reticulum retention) also possessed by the functional domains of PE. Additionally, the PE-like chimeric immunogens of this invention possess a domain that functionalizes a domain of PE for which no function yet has been identified. Namely, PE-like chimeric immunogens replace the Ib domain of PE with a functional non-native epitope domain that serves as an immunogen to elicit an immune response against the non-native epitope.

Accordingly, PE-like chimeric immunogens include the following structural domains comprised of amino acid sequences, the domains imparting particular functions to the chimeric protein: (1) a "cell recognition domain" that functions as a ligand for a cell surface receptor and that mediates binding of the protein to a cell; (2) a "translocation domain" that mediates translocation from the endosomes to the cytosol; (3) a "non-native epitope domain" that contains the immunogenic non-native epitope; and, optionally, (4) an "endoplasmic reticulum ("ER") retention domain" that functions to translocate the molecule from the endosome to the endoplasmic reticulum, from which it enters the cytosol. When the ER retention domain is eliminated the chimeric immunogen still can retain immunogenic function.

In one embodiment, a PE-like chimeric immunogen comprises the native sequence of PE, except for the Ib domain, which is engineered to include the amino acid sequence of a non-native epitope. For example, one can insert an amino acid sequence encoding the non-native epitope into the cysteine-cysteine loop of the Ib domain. However, the relationship of PE structure to its function has been extensively studied. The amino acid sequence of PE has been re-engineered to provide new functions, and many amino acids or peptide segments critical and non-critical to PE function have been identified. The PE-like chimeric immunogens of this invention can incorporate these structural modifications to PE.

B. Cell Recognition Domain

The *Pseudomonas* exotoxin chimeras of this invention comprise an amino acid sequence encoding a "cell recognition domain." The cell recognition domain functions as a ligand for a cell surface receptor. It mediates binding of the protein to a cell. Its purpose is to target the chimera to a cell which will transport it to the cytosol for processing. The cell recognition domain can be located in the position of domain Ia of PE. However, this domain can be moved out of the normal organizational sequence. More particularly, the cell recognition domain can be inserted upstream of the ER retention domain. Alternatively the cell recognition domain can be chemically coupled to the toxin. Also, the chimera can include a first cell recognition domain at the location of the Ia domain and a second cell recognition domain upstream of the ER retention domain. Such constructs can bind to more than one cell type. See, e.g., R. J. Kreitman et al. (1992) *Bioconjugate Chem.* 3:63-68.

Because the cell recognition domain functions as a handle to attach the chimera to a cell, it can have the structure of any polypeptide known to bind to a particular receptor. Accordingly, the domain generally has the size of known polypeptide ligands, e.g., between about 10 amino acids and about 1500 amino acids, or about 100 amino acids and about 300 amino acids.

Several methods are useful for identifying functional cell recognition domains for use in chimeric immunogens. One method involves detecting binding between a chimera that comprises the cell recognition domain with the receptor or with a cell bearing the receptor. Other methods involve detecting entry of the chimera into the cytosol, indicating that the first step, cell binding, was successful. These methods are described in detail below in the section on testing.

The cell recognition domain can have the structure of any polypeptide that binds to a cell surface receptor. In one embodiment, the amino acid sequence is that of domain Ia of PE, thereby targeting the chimeric protein to the α2-MR domain. In other embodiments domain Ia can be substituted with: growth factors, such as TGFα, which binds to epidermal growth factor ("EGF"); IL-2, which binds to the IL-2 receptor; IL-6, which binds to the IL-6 receptor (e.g., activated B cells and liver cells); CD4, which binds to HIV-infected cells); a chemokine (e.g., Rantes, MIP-1α or MIP-1β), which binds to a chemokine receptor (e.g., CCR5 or fusin (CXCR4)); ligands for leukocyte cell surface receptors, for example, GM-CSF, G-CSF; ligands for the IgA receptor; or antibodies or antibody fragments directed to any receptor (e.g., single chain antibodies against human transferrin receptor). I. Pastan et al. (1992) *Annu. Rev. Biochem.* 61:331-54.

In one embodiment, the cell recognition domain is located in place of domain Ia of PE. It can be attached to the other moiety of the molecule through a linker. However, engineering studies show that *Pseudomonas* exotoxin can be targeted to certain cell types by introducing a cell recognition domain upstream of the ER retention sequence, which is located at the carboxy-terminus of the polypeptide. For example, TGFα has been inserted into domain III just before amino acid 604, i.e., about ten amino acids from the carboxy-terminus. This chimeric protein binds to cells bearing EGF receptor. Pastan et al., U.S. Pat. No. 5,602,095.

Cell specific ligands which are proteins can often be formed in part or in whole as a fusion protein with the *Pseudomonas* exotoxin chimeras of the present invention. A "fusion protein" refers to a polypeptide formed by the joining of two or more polypeptides through a peptide bond formed by the amino terminus of one polypeptide and the carboxyl terminus of the other polypeptide. The fusion protein may be formed by the chemical coupling of the constituent polypeptides but is typically expressed as a single polypeptide from a nucleic acid sequence encoding the single contiguous fusion protein. Included among such fusion proteins are single chain Fv fragments (scFv). Particularly preferred targeted *Pseudomonas* exotoxin chimeras are disulfide stabilized proteins which can be formed in part as a fusion protein as exemplified herein. Other protein cell specific ligands can be formed as fusion proteins using cloning methodologies well known to the skilled artisan.

Attachment of cell specific ligands also can be accomplished through the use of linkers. The linker is capable of forming covalent bonds or high-affinity non-covalent bonds to both molecules. Suitable linkers are well known to those of ordinary skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine).

In one embodiment, domain Ia is replaced with a polypeptide sequence for an immunoglobulin heavy chain from an immunoglobulin specific for the target cell. The light chain of the immunoglobulin can be co-expressed with the PE-like chimeric immunogen so as to form a light chain-heavy chain dimer. In the conjugate protein, the antibody is chemically linked to a polypeptide comprising the other domains of the chimeric immunogen.

The procedure for attaching a *Pseudomonas* exotoxin chimera to an antibody or other cell specific ligand will vary according to the chemical structure of the toxin. Antibodies contain a variety of functional groups; e.g., sulfhydryl (—S), carboxylic acid (COOH) or free amine (—$NH_2$) groups, which are available for reaction with a suitable functional group on a toxin. Additionally, or alternatively, the antibody or *Pseudomonas* exotoxin chimera can be derivatized to expose or attach additional reactive functional groups. The derivatization may involve attachment of any of a number of linker molecules such as those available from Pierce Chemical Company, Rockford Ill.

A bifunctional linker having one functional group reactive with a group on the *Pseudomonas* exotoxin chimera, and another group reactive with a cell specific ligand, can be used to form a desired conjugate. Alternatively, derivatization may involve chemical treatment of the *Pseudomonas* exotoxin chimera or the cell specific ligand, e.g., glycol cleavage of the sugar moiety of a glycoprotein antibody with periodate to generate free aldehyde groups. The free aldehyde groups on the antibody may be reacted with free amine or hydrazine groups on the antibody to bind the *Pseudomonas* exotoxin chimera thereto. (See J. D. Rodwell et al., U.S. Pat. No. 4,671,958.) Procedures for generation of free sulfhydryl groups on antibodies or other proteins, are also known. (See R. A. Nicoletti et al., U.S. Pat. No. 4,659,839.)

C. Translocation Domain

PE-like chimeric immunogens also comprise an amino acid sequence encoding a "PE translocation domain." The PE translocation domain comprises an amino acid sequence sufficient to effect translocation of chimeric proteins that have been endocytosed by the cell into the cytosol. The amino acid sequence is identical to, or substantially identical to, a sequence selected from domain II of PE.

The amino acid sequence sufficient to effect translocation can derive from the translocation domain of native PE. This domain spans amino acids 253-364. The translocation domain can include the entire sequence of domain II. However, the entire sequence is not necessary for translocation. For example, the amino acid sequence can minimally contain, e.g., amino acids 280-344 of domain II of PE. Sequences outside this region, i.e., amino acids 253-279 and/or 345-364, can be eliminated from the domain. This domain also can be engineered with substitutions so long as translocation activity is retained.

The translocation domain functions as follows. After binding to a receptor on the cell surface, the chimeric proteins enter the cell by endocytosis through clathrin-coated pits. Residues 265 and 287 are cysteines that form a disulfide loop. Once internalized into endosomes having an acidic environment, the peptide is cleaved by the protease furin between Arg279 and Gly280. Then, the disulfide bond is reduced. A mutation at Arg279 inhibits proteolytic cleavage and subsequent translocation to the cytosol. M. Ogata et al. (1990) *J. Biol. Chem.* 265:20678-85. However, a fragment of PE containing the sequence downstream of Arg279 (called "PE37") retains substantial ability to translocate to the cytosol. C. B. Siegall et al. (1989) *J. Biol. Chem.* 264:14256-61. Sequences in domain II beyond amino acid 345 also can be deleted without inhibiting translocation. Furthermore, amino acids at positions 339 and 343 appear to be necessary for translocation. C. B. Siegall et al. (1991) *Biochemistry* 30:7154-59.

Methods for determining the functionality of a translocation domain are described below in the section on testing.

D. Non-Native Epitope Domain

PE-like chimeric immunogens also comprise an amino acid sequence encoding a "non-native epitope domain." The non-native epitope domain comprises the amino acid sequence of a non-native epitope. The domain functions to contain the immunogenic non-native epitope for presentation to the immune system. The non-native epitope domain is engineered into the Ib domain location of PE, between the translocation domain (e.g., domain II) and the ER retention domain (e.g., domain III). Methods of determining immunogenicity of a translocation domain are described below in the section on testing.

The non-native epitope can be any amino acid sequence that is immunogenic. The non-native epitope domain can have between about 5 amino acids and about 1500 amino acids. This includes domains having between about 15 amino acids and about 350 amino acids or about 15 amino acids and about 50 amino acids.

In native *Pseudomonas* exotoxin A, domain Ib spans amino acids 365 to 399. The native Ib domain is structurally characterized by a disulfide bond between two cysteines at positions 372 and 379. Domain Ib is not essential for cell binding, translocation, ER retention or ADP ribosylation activity. Therefore, it can be entirely re-engineered.

The non-native epitope domain can be linear or it can include a cysteine-cysteine loop that comprises the non-native epitope. In one embodiment, the non-native epitope domain includes a cysteine-cysteine loop that comprises the non-native epitope. This arrangement offers several advantages. First, when the non-native epitope naturally exists inside, or comprises, a cysteine-cysteine disulfide bonded loop, the non-native epitope domain will present the epitope in near-native conformation. Second, it is believed that charged amino acid residues in the native Ib domain result in a hydrophilic structure that sticks out away from the molecule and into the solvent, where it is available to interact with immune system components. Therefore, placing the non-native epitope within a cysteine-cysteine loop results in more effective presentation when the non-native epitope also is hydrophilic. Third, the Ib domain is highly insensitive to mutation. Therefore, although the cysteine-cysteine loop of the native Ib domain has only six amino acids between the cysteine residues, one can insert much longer sequences into the loop without disrupting cell binding, translocation, ER retention or ADP ribosylation activity.

This invention envisions several ways in which to engineer the non-native epitope domain into the Ib domain location. One method involves inserting the amino acid sequence of the non-native epitope directly into the amino acid sequence of the Ib domain, with or without deletion of native amino acid sequences. Another method involves removing all or part of the Ib domain and replacing it with an amino acid sequence that includes the non-native epitope between two cysteine residues so that the cysteines engage in a disulfide bond when the protein is expressed. For example, if the non-native epitope normally exists within a cysteine-cysteine loop structure of a polypeptide, a portion of the polypeptide that includes the loop and the non-native epitope can be inserted in place of the cysteine-cysteine loop domain.

The choice of the non-native epitope is at the discretion of the practitioner. In choosing, the practitioner may consider the following. While the non-native epitope domain can be linear, non-native epitopes that naturally exist within a cysteine-cysteine loop take advantage of the natural structure of the Ib loop of *Pseudomonas* exotoxin A. Epitopes from agents responsible for indolent infections or cancer-specific antigens are attractive because these antigens tend to resist attack from the immune system. Also, recombinant technology allows one to quickly insert a polynucleotide encoding an epitope into a vector encoding the chimeric protein. Therefore, one can quickly change sequences as a non-native epitope changes. Accordingly, epitopes from rapidly evolving infectious agents make attractive inserts.

Thus, for example, epitopes can be chosen from any pathogen, e.g., viruses, bacteria and protozoan parasites. Viral sources of epitopes include, for example, HIV, herpes zoster, influenza, polio and hepatitis. Bacterial sources include, for example, tuberculosis, *Chlamydia* or *Salmonella*. Parasitic protozoan sources include, for example, *Trypanosoma* or *Plasmodium*. In particular, the agent can be one that gains entry into the body through epithelial mucosal membranes. Useful cancer-specific antigens include those that are expressed on the cell surface and, therefore, can be target of a cytotoxic T-lymphocyte response, such as a prostate cancer-specific marker (e.g., PSA), a breast cancer-specific marker (e.g., BRCA-1 or HER2), a pancreatic cancer-specific marker (e.g., CA9-19), a melanoma marker (e.g., tyrosinase) or a cancer-specific mutant form of EGF.

In one embodiment, the non-native epitope derives from the principal neutralizing loop of a retrovirus, such as HIV-1 or HIV-2. In particular, the epitope can derive from the V3 loop of gp120 protein from HIV-1. A neutralizing loop can be identified by neutralizing antibodies, i.e., antibodies that neutralize infectivity of the virus. The sequences can be from any strain, in particular, circulating strains. Such strains include, for example, MN (e.g., subtype B) or Thai-E (e.g., subtype E). V3 loops of various strains of HIV-1 have about 35 amino acids. The strains of HIV can be T-cell tropic or macrophage tropic. In one embodiment, the sequences from the V3 loop include at least 8 amino acids (e.g., a peptide sufficiently long to fit into an MHC Class II binding pocket) that includes a V3 loop apex. The V3 loop of MN strain of HIV has the sequence: CTRPNYNKRK RIHIG PGRAF YTTKNIIGTI RQAHC (SEQ ID NO:3). The V3 loop of Thai-E strain of HIV has the sequence: CTRPSNNTRT SITIGPGOVE YRTGDIIGDI RKAYC (SEQ ID NO:4). The V3 loop apex is underlined. The sequence be around 14 to around 26 amino acids long. A vaccine can comprise a plurality of immunogens having different viral epitopes.

In another embodiment the non-native epitope can be an epitope expressed by a cell during disease. For example, the non-native epitope can be a cancer cell marker. For example, certain breast cancers express a mutant EGF ("epidermal growth factor") receptor that results from a splice variant. This mutant form exhibits a unique epitope.

E. ER Retention Domain

PE-like chimeric immunogens also can comprise an amino acid sequence encoding an "endoplasmic reticulum retention domain." The endoplasmic reticulum ("ER") retention domain functions in translocating the chimeric protein to from the endosome to the endoplasmic reticulum, from where it is transported to the cytosol. The ER retention domain is located at the position of domain III in PE. The ER retention domain comprises an amino acid sequence that has, at its carboxy terminus, an ER retention sequence. The ER retention sequence in native PE is REDLK (SEQ ID NO:11). Lysine can be eliminated (i.e., REDL (SEQ ID NO:12)) without a decrease in activity. REDLK (SEQ ID NO:11) can be replaced with other ER retention sequences, such as KDEL (SEQ ID NO:13), or polymers of these sequences. M. Ogata et al. (1990) *J. Biol. Chem.* 265:20678-85. Pastan et al., U.S. Pat. No. 5,458,878. I. Pastan et al. (1992) *Annu. Rev. Biochem.* 61:331-54.

Sequences up-stream of the ER retention sequence can be the native PE domain III (preferably de-toxified), can be entirely eliminated, or can be replaced by another amino acid sequence. If replaced by another amino acid sequence, the sequence can, itself, be highly immunogenic or can be slightly immunogenic. A highly immunogenic ER retention domain is preferable for use in eliciting a humoral immune response. Chimeras in which the ER retention domain is only slightly immunogenic will be more useful when an MHC Class I-dependent cell-mediated immune response is desired.

Activity of this domain can be assessed by testing for translocation of the protein into the target cell cytosol using the assays described below.

In native PE, the ER retention sequence is located at the carboxy terminus of domain III. Domain III has two functions in PE. It exhibits ADP-ribosylating activity and directs endocytosed toxin into the endoplasmic reticulum. Eliminating the ER retention sequence from the chimeric protein does not alter the activity of *Pseudomonas* exotoxin as a superantigen, but does inhibit its utility to elicit an MHC Class I-dependent cell-mediated immune response.

The ribosylating activity of PE is located between about amino acids 400 and 600 of PE. In methods of vaccinating a subject using the chimeric proteins of this invention, it is preferable that the protein be non-toxic. One method of doing so is by eliminating ADP ribosylation activity. In this way, the chimeric protein can function as a vector for non-native epitope sequences to be processed by the cell and presented on the cell surface with MHC Class I molecules, rather than as a toxin. ADP ribosylation activity can be eliminated by, for example, deleting amino acid E553 ("ΔE553"). M. Lukac et al. (1988) *Infect. and Immun.* 56:3095-3098. Alternatively, the amino acid sequence of domain III, or portions of it, can be deleted from the protein. Of course, an ER retention sequence should be included at the carboxy-terminus.

In one embodiment, the sequence of the ER retention domain is substantially identical to the native amino acid sequences of the domain III, or a fragment of it. In one embodiment, the ER retention domain is domain III of PE.

In another embodiment, a cell recognition domain is inserted into the amino acid sequence of the ER retention domain (e.g., into domain III). For example, the cell recognition domain can be inserted just up-stream of the ER retention sequence, so that the ER retention sequence is connected directly or within ten amino acids of the carboxy terminus of the cell recognition domain.

F. Methods of Making PE-Like Chimeric Immunogens

PE-like chimeric immunogens preferably are produced recombinantly, as described below. This invention also envisions the production of PE chimeric proteins by chemical synthesis using methods available to the art.

G. Testing PE-Like Immunogenic Chimeras

Having selected various structures as domains of the chimeric immunogen, the function of these domains, and of the chimera as a whole, can be tested to detect functionality. PE-like immunogenic chimeras can be tested for cell recognition, cytosolic translocation and immunogenicity using routine assays. The entire chimeric protein can be tested, or, the function of various domains can be tested by substituting them for native domains of the wild-type toxin.

1. Receptor Binding/Cell Recognition

The function of the cell binding domain can be tested as a function of the chimera to bind to the target receptor either isolated or on the cell surface.

In one method, binding of the chimera to a target is performed by affinity chromatography. For example, the chimera can be attached to a matrix in an affinity column, and binding of the receptor to the matrix detected.

Binding of the chimera to receptors on cells can be tested by, for example, labeling the chimera and detecting its binding to cells by, e.g., fluorescent cell sorting, autoradiography, etc.

If antibodies have been identified that bind to the ligand from which the cell recognition domain is derived, they also are useful to detect the existence of the cell recognition domain in the chimeric immunogen by immunoassay, or by competition assay for the cognate receptor.

2. Translocation to the Cytosol

The function of the translocation domain and the ER retention domain can be tested as a function of the chimera's ability to gain access to the cytosol. Because access first requires binding to the cell, these assays also are useful to determine whether the cell recognition domain is functioning.

a. Presence in the Cytosol

In one method, access to the cytosol is determined by detecting the physical presence of the chimera in the cytosol. For example, the chimera can be labelled and the chimera exposed to the cell. Then, the cytosolic fraction is isolated and the amount of label in the fraction determined. Detecting label in the fraction indicates that the chimera has gained access to the cytosol.

b. ADP Ribosylation Activity

In another method, the ability of the translocation domain and ER retention domain to effect translocation to the cytosol can be tested with a construct containing a domain III having ADP ribosylation activity. Briefly, cells are seeded in tissue culture plates and exposed to the chimeric protein or to an engineered PE exotoxin containing the modified translocation domain or ER retention sequence in place of the native domains. ADP ribosylation activity is determined as a function of inhibition of protein synthesis by, e.g., monitoring the incorporation of $^3$H-leucine.

3. Immunogenicity

The function of the non-native epitope can be determined by determining humoral or cell-mediated immunogenicity. Immunogenicity can be tested by several methods. Humoral immune response can tested by inoculating an animal and detecting the production of antibodies against the foreign immunogen. Cell-mediated cytotoxic immune responses can be tested by immunizing an animal with the immunogen, isolating cytotoxic T cells, and detecting their ability to kill cells whose MHC Class I molecules bear amino acid sequences from the non-native epitope. Because generating a cytotoxic T cell response requires both binding of the chimera to the cell and translocation to the cytosol, this test also tests the activity of the cell recognition domain, the translocation domain and the ER retention domain.

III. Recombinant Polynucleotides Encoding PE-Like Chimeric Immunogens

A. Recombinant Polynucleotides

1. Sources

This invention provides recombinant polynucleotides comprising a nucleotide sequence encoding the PE-like chimeric immunogens of this invention. These polynucleotides are useful for making the PE-like chimeric immunogens. In another aspect, this invention provides a PE-like protein cloning platform comprising a recombinant polynucleotide sequence encoding a cell recognition domain, a translocation domain, an ER retention domain and, between the translocation domain and the ER retention domain, a cloning site for a polynucleotide sequence encoding a non-native epitope domain.

The recombinant polynucleotides of this invention are based on polynucleotides encoding *Pseudomonas* exotoxin A, or portions of it. A nucleotide sequence encoding PE is presented above. The practitioner can use this sequence to prepare PCR primers for isolating a full-length sequence. The sequence of PE can be modified to engineer a polynucleotide encoding the PE-like chimeric immunogen or platform.

A polynucleotide encoding PE or any other polynucleotide used in the chimeric proteins of the invention can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of PE or a cell recognition molecule.

A wide variety of cloning and in vitro amplification methodologies are well-known to persons skilled in the art. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

2. Mutagenized Versions

Mutant versions of the proteins can be made by site-specific mutagenesis of other polynucleotides encoding the proteins, or by random mutagenesis caused by increasing the error rate of PCR of the original polynucleotide with 0.1 mM MnCl$_2$ and unbalanced nucleotide concentrations.

Eliminating nucleotides encoding amino acids 1-252 yields a construct referred to as "PE40." Eliminating nucleotides encoding amino acids 1-279 yields a construct referred to as "PE37." (See Pastan et al., U.S. Pat. No. 5,602,095.) The practitioner can ligate sequences encoding cell recognition domains to the 5' end of these platforms to engineer PE-like chimeric proteins that are directed to particular cell surface receptors. These constructs optionally can encode an amino-terminal methionine. A cell recognition domain can be inserted into such constructs in the nucleotide sequence encoding the ER retention domain.

3. Chimeric Protein Cloning Platforms

A cloning site for the non-native epitope domain can be introduced between the nucleotides encoding the cysteine residues of domain Ib. For example, as described in the Examples, a nucleotide sequence encoding a portion of the Ib domain between the cysteine-encoding residues can be removed and replaced with a nucleotide sequence encoding an amino acid sequence and that includes a PstI cloning site. A polynucleotide encoding the non-native epitope and flanked by PstI sequences can be inserted into the vector.

The construct also can be engineered to encode a secretory sequence at the amino terminus of the protein. Such constructs are useful for producing the immunogens in mammalian cells. In vitro, such constructs simplify isolation of the immunogen. In vivo, the constructs are useful as polynucleotide vaccines; cells that incorporate the construct will express the protein and secrete it where it can interact with the immune system.

B. Expression Vectors

This invention also provides expression vectors for expressing PE-like chimeric immunogens. Expression vectors are recombinant polynucleotide molecules comprising expression control sequences operatively linked to a nucleotide sequence encoding a polypeptide. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc.) Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes.

Expression vectors useful in this invention depend on their intended use. Such expression vectors must, of course, contain expression and replication signals compatible with the host cell. Expression vectors useful for expressing PE-like chimeric immunogens include viral vectors such as retroviruses, adenoviruses and adeno-associated viruses, plasmid vectors, cosmids, and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also Inouye et al., U.S. Pat. No. 5,272,065; *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

C. Recombinant Cells

The invention also provides recombinant cells comprising an expression vector for expression of the nucleotide sequences encoding a PE chimeric immunogen of this invention. Host cells can be selected for high levels of expression in order to purify the protein. The cells can be prokaryotic cells, such as *E. coli*, or eukaryotic cells. Useful eukaryotic cells include yeast and mammalian cells. The cell can be, e.g., a recombinant cell in culture or a cell in vivo.

*E. coli* has been successfully used to produce PE-like chimeric immunogens. The protein can fold and disulfide bonds can form in this cell.

IV. *Pseudomonas* Exotoxin A-Like Chimeric Immunogen Vaccines

PE-like chimeric immunogens are useful in vaccines for eliciting a protective immune response against agents bearing the non-native epitope. A vaccine can include one or a plurality (i.e. a multivalent vaccine) of different PE-like chimeric immunogens. For example, a vaccine can include PE-like chimeric immunogens whose non-native epitopes come from several circulating strains of a pathogen. As the pathogen evolves, new PE-like chimeric immunogens can be constructed that include the altered epitopes, for example, from breakthrough viruses. In one embodiment, the vaccine comprises epitopes from a T-cell-tropic virus and from a macrophage-tropic virus. For example, a vaccine against HIV infection can include immunogens whose non-native epitopes derive from the V3 loop of MN and Thai-E strains of HIV. Also, the epitopes can derive from any peptide from HIV that is involved in membrane fusion, e.g., gp120 or gp41. Alternatively, because they are subunit vaccines, the vaccine can include PE-like chimeric immunogens whose non-native epitopes are selected from various epitopes of the same pathogen.

The vaccine can come lyophilized or already reconstituted in sterile solution for use. An immunizing dose is between about 1 µg and about 1000 µg, more usually between about 10 µg and about 50 µg of the recombinant protein. For determination of immunizing doses see, for example, *Manual of Clinical Immunology*, H. R. Rose and H. Friedman, American Society for Microbiology, Washington, D.C. (1980). A unit dose is about 0.05 ml to about 1 ml, more usually about 0.5 ml. A dose is preferably delivered subcutaneously or intramuscularly. An injection can be followed by several more injections spaced about 4 to about 8 weeks apart. Booster doses can follow in about 1 to about 10 years. The vaccine can be prepared in dosage forms containing between 1 and 50 doses (e.g., 0.5 ml to 25 ml), more usually between 1 and 10 doses (e.g., 0.5 ml to 5 ml). The vaccine also can include an adjuvant, that potentiates an immune response when used in conjunction with an antigen. Useful adjuvants include alum, aluminum hydroxide or aluminum phosphate.

V. Methods of Eliciting an Immune Response

PE-like chimeric immunogens are useful in eliciting an immune response against antigens bearing the non-native epitope. Eliciting a humoral immune response is useful in the production of antibodies that specifically recognize the non-native epitope and in immunization against cells, viruses or other agents that bear the non-native epitope. PE-like chimeric immunogens are also useful in eliciting MHC Class I-dependent or MHC Class II-dependent cell-mediated immune responses. They are also useful in eliciting a secretory immune response.

A. Prophylactic and Therapeutic Treatments

PE-like chimeric immunogens can include non-native epitopes from pathogenic organisms or from pathological cells from a subject, such as cancer cells. Accordingly, this invention provides prophylactic and therapeutic treatments for diseases involving the pathological activity of agents, either pathogens or aberrant cells, that bear the non-native epitope. The methods involve immunizing a subject with PE-like chimeric immunogens bearing the non-native epitope. The resulting immune responses mount an attack against the pathogens, themselves, or against cells that express the non-native epitope. For example, if the pathology results from bacterial or parasitic protozoan infection, the immune system mounts a response against the pathogens, themselves. If the pathogen is a virus, infected cells will express the non-native epitope on their surface and become the target of a cytotoxic response. Aberrant cells, such as cancer cells, often express un-normal epitopes, and also can be subject to a cytotoxic immune response.

B. Humoral Immune Response

PE-like chimeric immunogens are useful in eliciting the production of antibodies against the non-native epitope by a subject. PE-like chimeric immunogens are attractive immunogens for making antibodies against non-native epitopes that naturally occur within a cysteine-cysteine loop: Because they contain the non-native epitope within a cysteine-cysteine loop, they present the epitope to the immune system in near-native conformation. The resulting antibodies generally recognize the native antigen better than those raised against linearized versions of the non-native epitope.

Methods for producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector, such as a recombinant vaccinia virus (see, U.S. Pat. No. 4,722,848) is mixed with an adjuvant. Animals are immunized with the mixture. An animal's immune response to the immunogenic preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, NY; and Harlow and Lane (1989) *Antibodies: A Laboratory Manual* Cold Spring Harbor Press, NY.

In various embodiments, the antibodies ultimately produced can be monoclonal antibodies, humanized antibodies, chimeric antibodies or antibody fragments.

Monoclonal antibodies are prepared from cells secreting the desired antibody. These antibodies are screened for binding to polypeptides comprising the epitope, or screened for agonistic or antagonistic activity, e.g., activity mediated through the agent comprising the non-native epitope. In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495-497.

In another embodiment, the antibodies are humanized immunoglobulins. Humanized antibodies are made by linking the CDR regions of non-human antibodies to human constant regions by recombinant DNA techniques. See Queen et al., U.S. Pat. No. 5,585,089.

In another embodiment of the invention, fragments of antibodies against the non-native epitope are provided. Typically, these fragments exhibit specific binding to the non-native epitope similar to that of a complete immunoglobulin. Antibody fragments include separate heavy chains, light chains, Fab, Fab' F(ab')$_2$ and Fv. Fragments are produced by recombinant DNA techniques, or by enzymic or chemical separation of intact immunoglobulins.

Other suitable techniques involve selection of libraries of recombinant antibodies in phage or similar vectors. See, Huse et al. (1989) *Science* 246: 1275-1281; and Ward et al. (1989) *Nature* 341: 544-546.

An approach for isolating DNA sequences which encode a human monoclonal antibody or a binding fragment thereof is by screening a DNA library from human B cells according to the general protocol outlined by Huse et al., *Science* 246:1275-1281 (1989) and then cloning and amplifying the sequences which encode the antibody (or binding fragment) of the desired specificity. The protocol described by Huse is rendered more efficient in combination with phage display technology. See, e.g., Dower et al., WO 91/17271 and McCafferty et al., WO 92/01047. Phage display technology can also be used to mutagenize CDR regions of antibodies previously shown to have affinity for the polypeptides of this invention or their ligands. Antibodies having improved binding affinity are selected.

The antibodies of this invention are useful for affinity chromatography in isolating agents bearing the non-native epitope. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified agents are released.

Antibodies were produced against gp120 using a PE-like chimeric immunogen having the gp120 V3 loop as the non-native epitope. The monoclonal antibodies selectively captured the soluble MN and Th-E chimeric proteins, confirming that the V3 loops were exposed and accessible to antibody probes. Also, sera from immunized rabbits neutralized HIV-1 infectivity in an in vitro assay.

C. MHC Class II-Dependent Cell-Mediated Immune Response

In another aspect, this invention provides methods for eliciting an MHC Class II-dependent immune response against cells expressing the non-native epitope. MHC Class II molecules bind peptides having particular amino acid motifs well known in the art. The MHC Class II-dependent response involves the uptake of an antigen by antigen-presenting cells (APC's), its processing, and presentation on the cell surface as part of an MHC Class II/antigenic peptide complex. Alternatively, MHC Class II molecules on the cell surface can bind peptides having the proper motif.

Antigen presenting cells interact with CD4-positive T-helper cells, thereby activating the T-helper cells. Activated T-helper cells stimulate B-lymphocytes to produce antibodies against the antigen. Antibodies mark cells bearing the antigen on their surface. The marked cells are subject to antibody-dependent cell-mediated cytotoxicity, in which NK cells or macrophages, which bear Fc receptors, attack the marked cells.

Methods for eliciting an MHC Class II-dependent immune response involve administering to a subject a vaccine including an immunogenic amount of a chimeric *Pseudomonas* exotoxin that includes an amino acid motif recognized by MHC Class II molecules of the subject. Alternatively, antigen presenting cells can be cultured with such peptides to allow binding, and the cells can be administered to the subject. Preferably, the cells are syngeneic with the subject.

D. MHC Class I-Dependent Cell-Mediated Immune Response

In another aspect, this invention provides methods for eliciting an MHC Class I-dependent cell-mediated immune response against cells expressing the non-native epitope in a subject. MHC Class I molecules bind peptides having particular amino acid motifs well known in the art. Proteins expressed in a cell are digested into peptides and presented on the cell surface in association with MHC Class I molecules. There, they are recognized by CD8-positive lymphocytes, generating a cytotoxic T-lymphocyte response against cells expressing the epitopes in association with MHC Class I molecules. Because CD4-positive T lymphocytes infected with HIV express gp120 and, thus, the V3 domain, the generation of cytotoxic T-lymphocytes that attack such cells is useful in the prophylactic or therapeutic treatment of HIV infections.

HLA-A1 binding motif includes a first conserved residue of T, S or M, a second conserved residue of D or E, and a third conserved residue of Y. Other second conserved residues are A, S or T. The first and second conserved residues are adjacent and are preferably separated from the third conserved residue by 6 to 7 residues. A second motif consists of a first conserved residue of E or D and a second conserved residue of Y where the first and second conserved residues are separated by 5 to 6 residues. The HLA-A3.2 binding motif includes a first conserved residue of L, M, I, V, S, A, T and F at position 2 and a second conserved residue of K, R or Y at the C-terminal end. Other first conserved residues are C, G or D and alternatively E. Other second conserved residues are H or F. The first and second conserved residues are preferably separated by 6 to 7 residues. The HLA-A11 binding motif includes a first conserved residue of T or V at position 2 and a C-terminal conserved residue of K. The first and second conserved residues are preferably separated by 6 or 7 residues. The HLA-A24.1 binding motif includes a first conserved residue of Y, F or W at position 2 and a C terminal conserved residue of F, I, W, M or L. The first and second conserved residues are preferably separated by 6 to 7 residues.

Another method involves transfecting cells ex vivo with such expression vectors, and administering the cells to the subject. The cells preferably are syngeneic to the subject.

Methods for eliciting an immune response against a virus in a subject are useful in prophylactic methods for preventing infection with the virus when the vaccine is administered to a subject who is not already infected.

E. IgA-Mediated Secretory Immune Response

Mucosal membranes are primary entryways for many infectious pathogens. Such pathogens include, for example, HIV, herpes, vaccinia, cytomegalovirus, *yersinia* and *vibrio*. Mucosal membranes include the mouth, nose, throat, lung, vagina, rectum and colon. As a defense against entry, the body secretes secretory IgA on the surfaces of mucosal epithelial membranes against pathogens. Furthermore, antigens presented at one mucosal surface can trigger responses at other mucosal surfaces due to trafficking of antibody-secreting cells between these mucosae. The structure of secretory IgA has been suggested to be crucial for its sustained residence and effective function at the luminal surface of a mucosa. As used herein, "secretory IgA" or "sIgA" refers to a polymeric molecule comprising two IgA immunoglobulins joined by a J chain and further bound to a secretory component. While mucosal administration of antigens can generate an IgG response, parenteral administration of immunogens rarely produce strong sIgA responses. Generating a secretory immune response for defense against HIV is a recognized need. (Bukawa, H., et al. 1995, *Nat Med* 1, 681-5; Mestecky, J., et. al., 1994, *Aids Res Hum Retroviruses* 10, S11-20.)

*Pseudomonas* exotoxin binds to receptors on mucosal membranes. Therefore, PE-like chimeric immunogens are an attractive vector for bringing non-native epitopes to a mucosal surface. There, the immunogens elicit an IgA-mediated immune response against the immunogen. Accordingly, this invention provides PE-like chimeric immunogens comprising a non-native epitope from a pathogen that gains entry through mucosal membranes. The cell recognition domain can be targeted to any mucosal surface receptor. These PE-like chimeric immunogens are useful for eliciting an IgA-mediated secretory immune response against immunogens that gain entry to the body through mucosal surfaces. PE-like chimeric immunogens used for this purpose should have ligands that bind to receptors on mucosal membranes as their cell recognition domains. For example, epidermal growth factor binds to the epidermal growth factor receptor on mucosal surfaces.

The immunogens can be applied to the mucosal surface by any of the typical means, including pharmaceutical compositions in the form of liquids or solids, e.g., sprays, ointments, suppositories or erodible polymers impregnated with the immunogen. Administration can involve applying the immunogen to a plurality of different mucosal surfaces in a series of immunizations, e.g., as booster immunizations. A booster inoculation also can be administered parenterally, e.g., subcutaneously. The immunogen can be administered in doses of about 1 µg to 1000 µg, e.g., about 10 µg to 100 µg.

Subcutaneous inoculation with vaccines comprising an epitope from the principal neutralizing domain of gp120 of HIV is not known to generate secretory IgA. Accordingly, mucosal presentation of the chimeric immunogens of this invention is useful for producing these hitherto unknown antibodies. This invention also provides secretory IgA that specifically recognize epitopes of other pathogens that enter the body through a mucous membrane.

The IgA response is strongest on mucosal surfaces exposed to the immunogen. Therefore, in one embodiment, the immunogen is applied to a mucosal surface that is likely to be a site of exposure to the particular pathogen. Accordingly, chimeric immunogens against sexually transmitted diseases can be administered to vaginal, anal or oral mucosal surfaces.

Mucosal administration of the chimeric immunogens of this invention result in strong memory responses, both for IgA and IgG. Therefore, in vaccination with them, it is useful to provide booster doses either mucosally or parenterally. The memory response can be elicited by administering a booster dose more than a year after the initial dose. For example, a booster dose can be administered about 12, about 16, about 20 or about 24 months after the initial dose.

VI. Polynucleotide Vaccines and Methods of Gene Therapy

Vaccines comprising polynucleotides encoding a protein immunogen, often called "DNA vaccines," offer certain advantages over polypeptide vaccines. DNA vaccines do not run the risk of contamination with unwanted protein immunogens. Upon administration to a subject, the polynucleotide is taken up by a cell. RNA is reverse transcribed into DNA. DNA is integrated into the genome in some percentage of transfected cells. Where the DNA integrates so as to be operatively linked with expression control sequences, or if such sequences are provided with the recombinant polynucleotide, the cell expresses the encoded polypeptide. Upon secretion from the cell, the polypeptide acts as an immunogen. Naked DNA is preferentially taken up by liver and by muscle cells. Accordingly, the polypeptide can be injected into muscle tissue, or provided by, e.g., biolistic injection. Generally, doses of naked polynucleotide will be from about 1 µg to 100 µg for a typical 70 kg patient.

The polynucleotide vaccines of this invention can include polynucleotides encoding PE-like chimeric immunogens that are used in polypeptide vaccines. This includes multiple immunogens including several variants of an epitope.

The following examples are offered by way of illustration, not by way of limitation.

EXAMPLES

I. Construction of PE-Like Chimeric Immunogens

To generate chimeric proteins, the subdomain Ib of ntPE was replaced with V3 loop sequences from either an MN (subtype B) or Thai-E subtype strain of HIV-1. The MN sequence is from a T-cell-tropic strain while the Thai-E sequence comes from a macrophage-tropic strain.

Wild-type (WT) PE is composed of 613 amino acids and has a molecular mass of 67,122 Da. Deletion of a glutamic acid 553 (ΔE553) results in a non-toxic version of PE (Lukac, M., et al., 1988, *Infect and Immun* 56:3095-3098), referred to as ntPE.

Plasmids were constructed by inserting oligonucleotide duplexes encoding V3 loop sequences into a new PE-based vector that was designed with a novel PstI site. In an effort to produce a V3 loop of similar topology to that found in gp120, the 14 or 26 amino acid inserts were flanked by cysteine residues (FIG. 1C—bold type). Construction of the novel vector resulted in several changes in the amino acid sequence of ntPE near the insertion point of the V3 loop (FIG. 1C—italics). The non-toxic chimeras, ntPE-V3MN14, ntPE-V3MN26 and ntPE-V3Th-E26, contained V3 loops of 14 or 26 amino acids from the MN strain or 26 amino acids from the Thai-E strain, respectively (nt="non-toxic"). Insertion of an irrelevant 16 amino acid sequence resulted in the construction of a control chimera referred to as ntPE-fp126. Removal of the Ib loop (6 amino acids) and modification of flanking amino acids adjacent to the V3 loop insert resulted in a small increase in molecular mass compared to wild-type PE (FIG. 1C).

More specifically, plasmid pMOA1A2VK352 (Ogata, M., et. al., 1992, *J Biol Chem,* 267, 25396-401), encoding PE, was digested with Sfi1 and ApaI (residues 1143 and 1275, respectively) and then re-ligated with a duplex containing a novel PstI site. The coding strand of the duplex had the following sequence: 5'-tggccctgac cctggccgcc gccgagagcg agcgcttcgt ccggcagggc accggcaacg acgaggccgg cgcggcaaac ctgcagggcc-3' (SEQ ID NO:5). The resulting plasmid encoded a slightly smaller version of PE and lacked much of domain Ib. The Pst1 site was then used to introduce duplexes encoding V3 loop sequences flanked by cysteine residues. To make non-toxic proteins, vectors were modified by the subcloning in an enzymatically inactive domain III from pVC45ΔE553. An additional subcloning, from pJH4 (Hwang, J., et. al., 1987, *Cell,* 48, 129-136), was needed to produce a vector that lacked a signal sequence. Insertion of duplexes and subcloning modifications were initially verified by restriction analysis while final constructs were confirmed by dideoxy double strand sequencing.

II. Characterization of Chimeras

A. Expression

All ntPE-V3 loop chimeric proteins were expressed in *E. coli* SA2821/BL21(λDE3) using a T7 promoter/T7 polymerase system (Studier, F. W., et. al., 1990, *Methods Enzymol* 185, 60-89). SA2821/BL21(λDE3) cells were transformed with the appropriate plasmid and grown to an absorbance of 1.0 (600 nm) in medium containing ampicillin. To induce high level protein expression, isopropyl-β-D-thiogalactoside (1 mM) was added to the culture and incubated for an additional 90 min. *E. coli* cell pellets, were resuspended in 50 mM Tris/20 mM EDTA, pH 8.0 (TE buffer) and dispersed using a Tissue Miser. Cell lysis was accomplished with lysozyme (200 μg/ml final concentration; Sigma) and membrane associated proteins were solubilized by the addition of 2.5% Triton X-100 and 0.5 M NaCl.

PE-V3 loop chimeras were present in inclusion bodies, which were recovered by centrifugation. After washing with TE containing 0.5% Triton X-100 and then with TE alone, inclusion bodies were solubilized by the addition of 6 M guanidine and 65 mM dithioerythritol. Refolding was allowed to proceed at a final protein concentration of 100 μg/ml for a minimum of 24 h at 8° C. in 0.1 M Tris (pH 8.0) containing 0.5 M L-arginine (Sigma), 2 mM EDTA and 0.9 mM glutathione. The protease inhibitor AEBSF (Boerhinger Mannheim) was added to a final concentration of 0.5 mM. Proteins were dialyzed against 20 mM Tris, 2 mM EDTA and 100 mM urea, pH 7.4. Following dialysis, proteins were applied to a Q sepharose column (Pharmacia Biotech; Piscataway, N.J.). After washing with 20 mM Tris (pH 8-0) containing 0.1 M NaCl, chimeric proteins were eluted with 0.3 M NaCl in the same buffer and concentrated using Centriprep-30 ultrafiltration devices (Amicon, Inc.; Beverly, Mass.). An HPLC gel filtration column (G3000SW from Toso Haas; Montgomeryville, Pa.) was used to isolate final products. A typical yield of properly folded protein per 4 L bacterial culture was 50-100 mg with a purity greater than 95%.

B. Biochemical Characterization

Chimeric proteins were separated by SDS-PAGE using 8-16% gradient polyacrylamide gels (Novex; San Diego, Calif.), and visualized by staining with Coomassie Blue. For Western blot analysis, proteins were transferred onto Immobilon-P membranes (Millipore Corp., Bedford, Mass.) and exposed to either an anti-PE mouse monoclonal antibody (M40-1 (Ogata, M., et. al., 1991, *Infect and Immun* 59, 407-414) or an anti-gp120 mouse monoclonal antibody (1F12 for MN sequences or 1B2 for Thai-E sequences; Genentech, Inc.; South San Francisco, Calif.). The primary antibody was detected by a secondary anti-mouse antibody conjugated to horseradish peroxidase. Reactive products were visualized by the addition of diaminobenzadine and hydrogen peroxide. Immunocapture experiments were performed for 30 min at 23° C. using the 1F12 anti-gp120 monoclonal antibody. Antibody-chimeric protein complexes were recovered with protein G sepharose beads (Pharmacia Biotech; Piscataway, N.J.) and separated using SDS-PAGE (as above). Recombinant forms of gp120 derived from HIV-1-MN (120/MN; Genentech, Inc.) and the That subtype E isolate (gp120/Th-E—Chiang Mai; Advanced Biotechnologies, Columbia Md.) were used as standards.

SDS-PAGE analysis of purified ntPE-V3 loop chimeras (FIG. 2A) was consistent with calculated masses (FIG. 1C). Western blots, using monoclonal antibodies raised against gp120/MN (1F12) or gp120/Th-E (1B2), showed strain-specific reactivity with the MN and Thai-E V3 loop chimeras (FIG. 2B).

Free sulfhydryl analysis of purified ntPE-V3 loop chimeras failed to demonstrate any unpaired cysteines, suggesting that the purified ntPE-V3 loop chimeras had refolded and oxidized to form a disulfide bond at the base of the V3 loop (FIG. 1A). The formation of this disulfide bond was expected to result in the exposure of the V3 loop at the surface of the chimeras.

To determine sulfhydryl content, chimeric proteins (15 mmols) in PBS (pH 7.4) containing 1 mM EDTA, were reacted with 1 mM thionitrobenzoate (DTNB) (Pierce Chem Co, Rockford, Ill.) for 15 min at 23° C. The release of thionitrobenzoate was monitored at 412 nm. DTNB reactivity was confirmed by the use of cysteine.

This was tested directly by immuno-capture studies (FIG. 2C). The 1F12 and 1B2 monoclonal antibodies selectively captured the soluble MN and Th-E chimeric proteins confirming that the V3 loops were exposed and accessible to antibody probes. Despite the fact that the 1F12 antibody reacted strongly with ntPE-V3MN14 in Western blots (FIG. 2B), it captured only a small amount of soluble protein (FIG. 2C, Lane 3), suggesting that the reactive epitope was not completely exposed when only 14 amino acids were inserted.

C. Circular Dichroism

To evaluate the impact of amino acid inserts on the secondary structure of the chimeras, near- and far-UV CD spectral analysis was performed on purified ntPE-V3MN14 and ntPE-V3MN26 proteins and compared these to wild-type PE (wtPE) spectra (FIGS. 3A and 3B). Circular dichroism (CD) spectra were collected on an Aviv 60DS spectropolarimeter. Near UV CD spectra (400 nm to 250 nm) were obtained in 0.2 nm increments with a 0.5 nm bandwidth and a 5 second time constant (150 readings/second averaged) for samples in a 1 cm pathlength cell. Far UV spectra (250 nm to 190 nm) were collected in 0.2 nm increments with a 0.5 nm bandwidth and a 3 second time constant in a 0.05 cm pathlength cell. Each spectrum was digitally smoothed using the Savitsky-Golay algorithm (Gorry, P. A. 1990, *Analytical Chem* 62, 570-573), corrected for concentration, and normalized to units of mean residue weight ellipticity (θMRW) using the following relationship:

$$\theta_{MRW} = \frac{\theta_{obs}(MW_{monomer}/n_{monomer})}{10(d)(c)}$$

where $\theta_{obs}$ is the observed ellipticity, $MW_{monomer}$ is the molecular weight of the monomer, $n_{monomer}$ is the number of amino acids in the monomer, d is the pathlength of the cell (cm), and c is the concentration of the sample in the cell (mg/ml).

Figure 3:
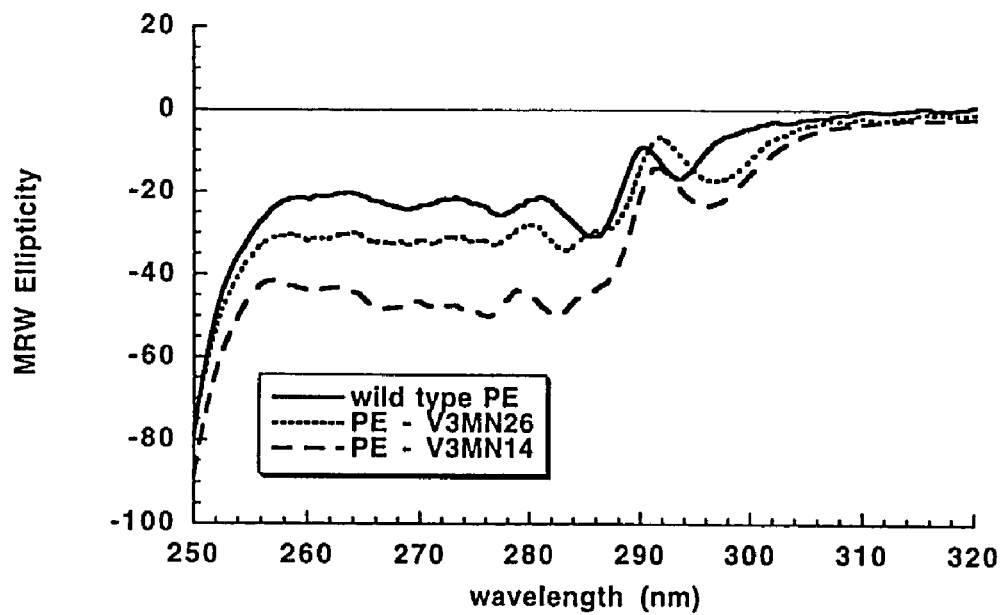
FIGS. 3A-3C. V3 loop amino acid sequence insertions do not significantly alter the secondary structure of wild-type PE. Near UV (A) and far UV (B) CD spectra (mean of three scans following background spectrum subtraction) were digitally smoothed, corrected for concentration, and normalized to units of mean residue weight ellipticity. (C) Secondary structure calculations were performed using the SEL-CON fitting program. *Calculated α-helix content agrees with values determined from changes in observed ellipticity at 222 nm.
Figure 3:
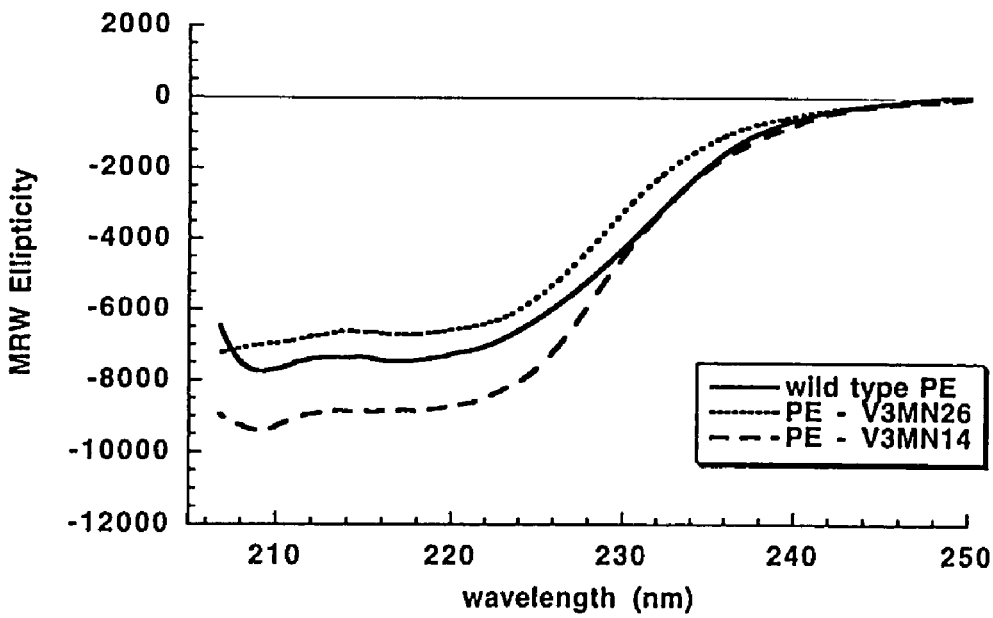

Secondary structure calculations (FIG. 3C) suggested that there were no significant differences between these proteins and wtPE. ntPE-V3MN14 demonstrated more negative ellipticity than ntPE-V3MN26 and wtPE, suggesting more strain may occur on the disulfide bond at the base of the loop insert for this chimera. Both ntPE-V3MN14 and ntPE-V3MN26 showed an apparent red-shift at 290 nm, possibly due to the additional tyrosine residues in the chimeras. Alternately, this red-shift could result from a slight environmental perturbation of a tryptophan residue. Altogether, these results suggest that the V3 loop inserts did not produce large alterations in the secondary structure relative to wild-type toxin and that the changes in tertiary structure were consistent with the presence of the 14 and 26 amino acid inserts.

III. Translocation to the Cytosol

After binding to the LRP receptor, ntPE-V3 loop chimeras should be endocytosed, cleaved by furin and the C-terminal portion containing domains II, the V3 loop and III should be translocated to the cytosol in a similar fashion to wtPE (Ogata, M., et. al., 1990, *Biol Chem* 265, 20678-85). This was tested directly by producing enzymatically active versions of PE-V3MN14 and 26 (containing glutamic acid 553 and having the ability to ADP-ribosylate elongation factor 2) and comparing their activity with wtPE in cytotoxicity assays.

Human A431 (epidermoid carcinoma) cells were seeded in 24-well tissue culture plates at $1\times10^5$ cells/well in RPMI 1640 media supplemented with 5% fetal bovine serum. After 24 h, cells were treated for 18 h at 37° C. with 4-fold dilutions of either wtPE or toxic forms (with a glutamic acid residue at position 553 and capable of ADP-ribosylating elongation factor 2) of the chimeric proteins. Inhibition of protein synthesis was assessed by monitoring the incorporation of $^3$H-leucine.

Figure 4:
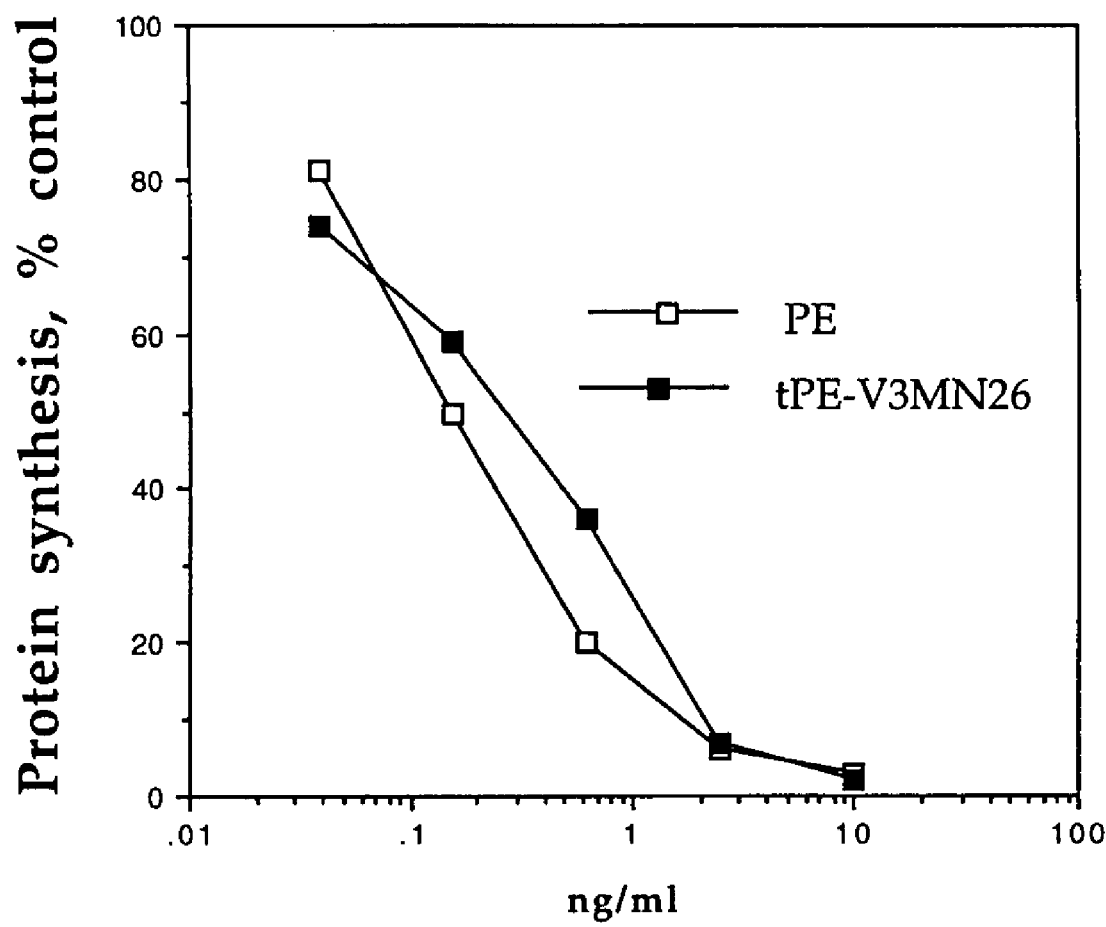
FIG. 4. Toxic PE-V3 loop chimeras affect cell survival. The extent of protein synthesis, assessed by $^3$H-leucine incorporation, was determined in human A431 cells following 18 h of exposure to various concentrations of either wild-type PE or a toxic form (with a glutamic acid residue at position 553 and capable of ADP ribosylating elongation factor 2) of PE-V3MN26.

When assayed for its ability to inhibit protein synthesis, PE-V3MN26 exhibited similar toxicity to wtPE in human A431 cells (FIG. 4). PE-V3MN14 was also fully toxic. These results confirmed that the size and location of the V3 loop inserts did not impede toxin delivery to the cytosol. Further, these data suggest that the isolation, refolding and purification protocol used to prepare these chimeras resulted in the production of a correctly folded and functional protein.

IV. Immunogenicity

To investigate their usefulness as immunogens, rabbits were injected subcutaneously with 200 μg of either the MN or Thai-E chimeras. Rabbits were immunized subcutaneously at four sites with 200 μg (total) of ntPE-V3MN26. The first injection was administered with complete Freund's adjuvant. All subsequent injections (at 2, 4 and 12 weeks) were given with incomplete Freund's adjuvant. Venous bleeds were obtained weekly after the third injection and screened by immunoblotting against gp120.

Figure 5A:
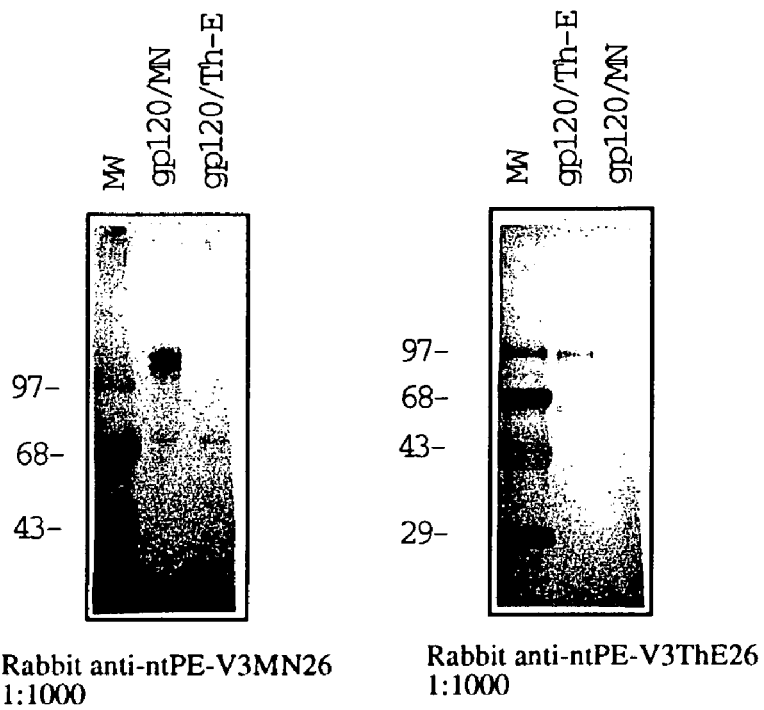
FIGS. 5A-5B. Characterization of rabbit sera following immunization with either ntPE-V3MN26 or ntPE-V3Th-E26. (A) Western blot reactivity of rabbit antisera diluted 1:1000 for recombinant gp120/MN and gp120/Th-E was assessed following SDS-PAGE and the transfer of proteins to Immobilon P membranes. Reactive primary antibody was detected by a secondary anti-rabbit antibody conjugated to horseradish peroxidase. (B) Rabbit sera obtained from animals injected with ntPE-V3MN26 was pre-incubated with competing soluble gp120/MN at concentrations up to 50 μg/ml. Residual reactivity was detected by Western blot analysis of immobilized gp120/MN as described for (A).

In Western blots, serum samples from rabbits immunized with the ntPE-V3MN proteins exhibited a strong reactivity for immobilized recombinant gp120/MN (FIG. 5A). Reactive titers increased with time: at 6 weeks reactivity was noted at 1:200 dilution, at 12 weeks at 1:5,000 dilution and at later times reactivity could be detected at 1:25,000. These anti-V3 loop/MN sera were not reactive with gp120/Thai-E (FIG. 5A). Sera from rabbits injected with non-toxic PE (i.e. ntPE with no insert) exhibited no reactivity for gp120. Rabbits injected with the ntPE-V3Th-E produced reactive sera for gp120/Thai-E but not for gp120/MN (FIG. 5A).

Figure 5B:
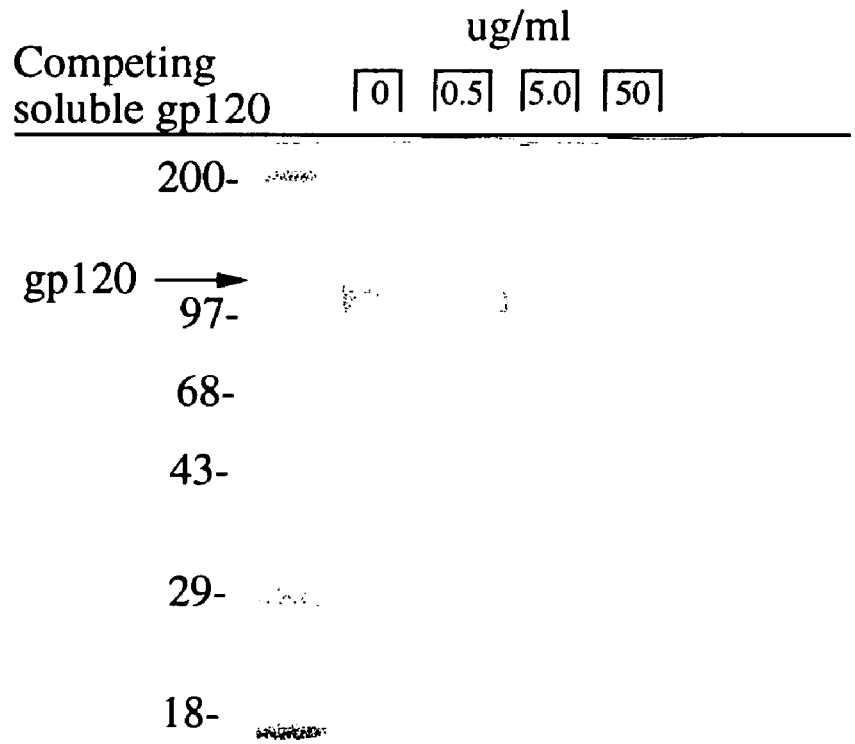

Sera from rabbits immunized with ntPE-V3MN26 were characterized further. Reactivity for immobilized gp120/MN was absorbed when these sera were pre-mixed with soluble recombinant gp120/MN (FIG. 5B). This blocking activity, which was dose-dependent and maximal at 50 μg/ml, indicated that rabbits responded primarily to V3 loop sequences that are exposed on the surface of gp120.

Figure 6:
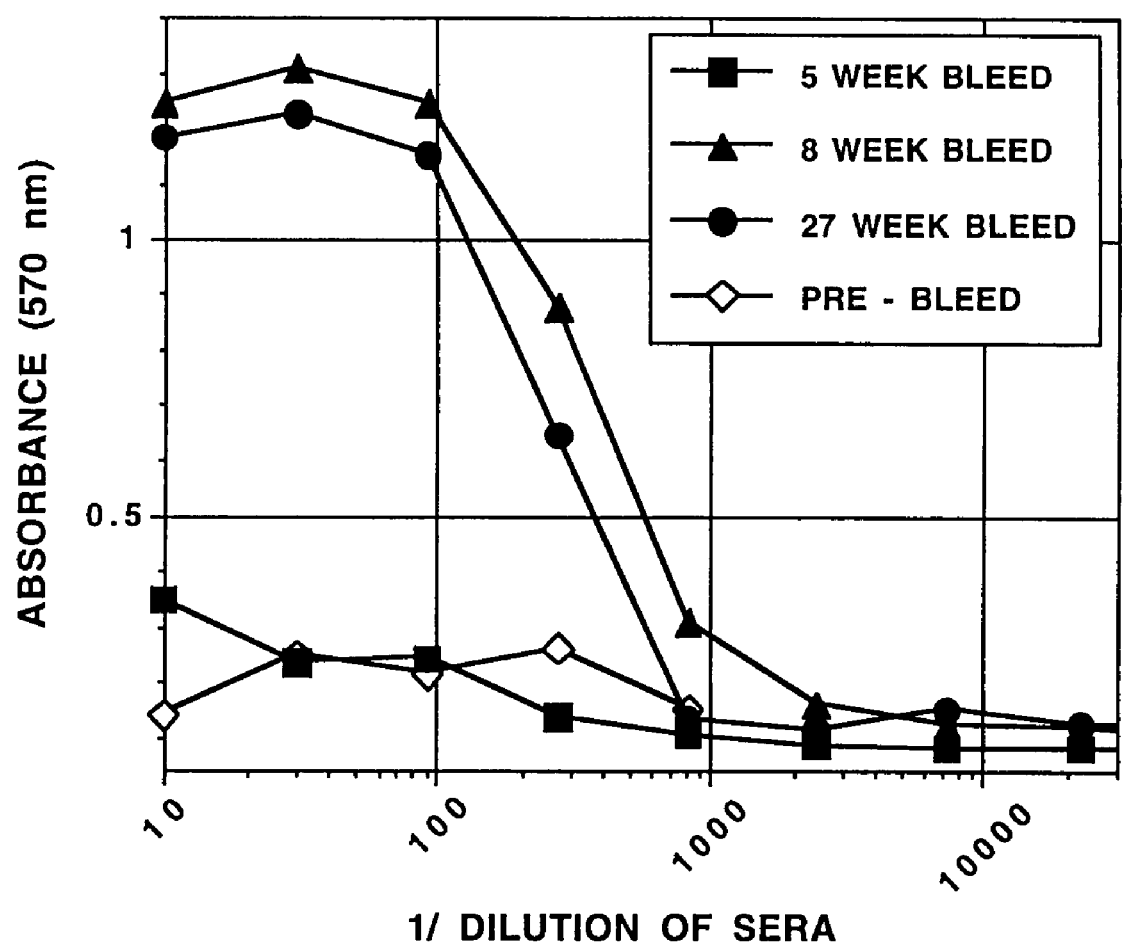
FIG. 6. A ntPE-V3 loop chimera administered to rabbits produces an antibody response capable of neutralizing HIV-1 infectivity in vitro. Rabbits were immunized subcutaneously with 200 μg ntPE-V3MN26 and boosted similarly after 2, 4 and 12 weeks. Sera collected up to 27 weeks after the initial administration were evaluated for the ability to protect a human T-cell line, MT4, from killing by HIV-1 MN as assessed by an MTT dye conversion assay. Values represent triplicate readings normalized against a control MT4 incubation not challenged by virus.
Figure 7:
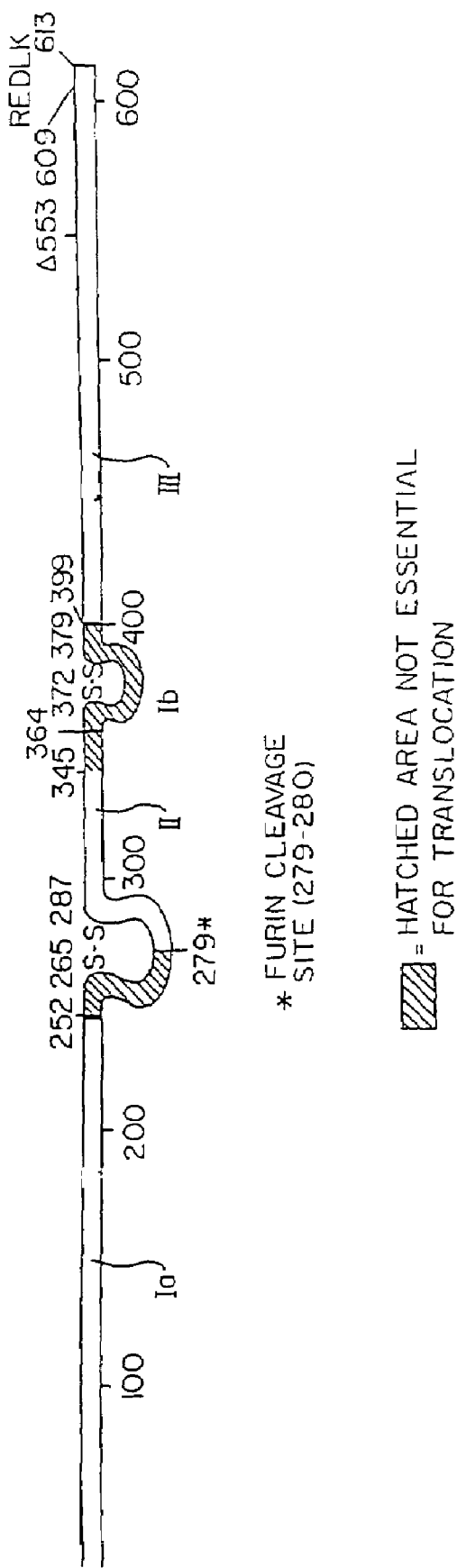
FIG. 7 is a diagram of *Pseudomonas* Exotoxin A structure. The amino acid position based on SEQ ID NO:2 is indicated. Domain 1a extends from amino acids 1-252. Domain II extends from amino acids 253-364. It includes a cysteine-cysteine loop formed by cysteines at amino acids 265-287. Furin cleaves within the cysteine-cysteine loop between amino acids 279 and 280. A fragment of PE beginning with amino acid 280 translocates to the cytosol. Constructs in which amino acids 345-364 are eliminated also translocate. Domain Ib spans amino acids 365-399. It contains a cysteine-cysteine loop formed by cysteines at amino acids 372 and 379. The domain can be eliminated entirely. Domain III spans amino acids 400-613. Deletion of amino acid 553 eliminates ADP ribosylation activity. The endoplasmic reticulum sequence, REDLK (SEQ ID NO: 11) is located at the carboxy-terminus of the molecule, from amino acid 609-613.

Sera from immunized rabbits were also found to neutralize HIV-1 infectivity in an in vitro assay (FIG. 6). This assay utilized MT4 cells as an indicator of HIV-1-mediated cell death (Miyoshi, I., et al., 1981, *Nature* 294, 770-1). Duplicate serial dilutions of antiserum was incubated with HIV-1/MN grown in FDA/H9 cells (Popovic, M., et al., 1984, *Science* 224, 497-500) and the mixture added to cells for 7 days. Viral-mediated cell death was assessed using a MTT dye assay (Robertson, G. A., et al., 1988, *J Virol Methods* 20, 195-202) and spectrophotometric analysis at 570 nm. The serum 50% inhibitory concentration was calculated and reported as the neutralization titer.

Pre-immune sera did not show any protection of a human T-cell line, MT4, from killing by HIV-1 MN. Although sera at 5 weeks following immunization also showed no protection, week 8 and week 27 sera were protective against viral challenge with 50% neutralization occurring at approximately a 1:400 dilution. Based upon the immunization schedule used, week 5 sera reflected the response in animals immunized and boosted once, while week 8 sera was from animals boosted twice and week 27 sera came from animals boosted three times. MT4 cell survival values obtained for sera dilutions of less that 1:100 for the week 8 and week 27 bleeds were greater than the unchallenged cell control used for normalization. This was likely due to stimulation by growth factors present in the rabbit sera. The data suggest that the immune response following subcutaneous injections of ntPE-V3 loop chimeras can result in the production of neutralizing antibodies.

V. Neutralization of Infectivity

Antibodies elicited by the chimeric immunogen were shown to have the ability to neutralize infectivity of HIV-1 in viral growth assays where suppression of p24 production was used as an indicator of HIV neutralization. Clinical isolates corresponding to subtype B, RVL05, and subtype E, Th92009, were incubated with dilutions of rabbit sera and cultured in PBMCs for a total of 5 days.

One assay utilized MT4 cells as an indicator of HIV-1-mediated cell death. I. Miyoshi et al. (1981) *Nature* 294: 770-771. Duplicate serial dilutions of antiserum were incubated with HIV-1/MN and grown in FDA/H9 cells and the mixture added to MT4 cells for 7 days. M. Popovic et al. (1984) *Science* 224:497-500. Viral-mediated cell death was assessed using a 3-(4,5-dimethylthiazol-2-yl)-2,5-diphenyltetrazolium bromide dye assay and spectrophotometric analysis at 570 nm. G. A. Robertson et al. (1988) *J. Virol. Methods* 20:195-202. The serum 50% inhibitory concentration was calculated and reported as the neutralization titer.

A second assay used p24 production of as an indicator of viral growth. T. Wrin et al. (1995) *J. Virol.* 69:39-48. Primary virus was first titrated to determine the amount that reproducibly yielded significant but submaximal amounts of p24. Virus preparations were incubated for 1 h at 37° C. with various dilutions of rabbit sera, either immune or pre-bleed, and this mixture was then added in quadruplicate to $2.5 \times 10^5$ PBMCs. The culture continued for 3 days at which time cells were washed and V3 Loop-Toxin Chimeras 9952 resuspended in medium containing interleukin 2. Accumulation of p24 was detected by an ELISA.

Figure 14:
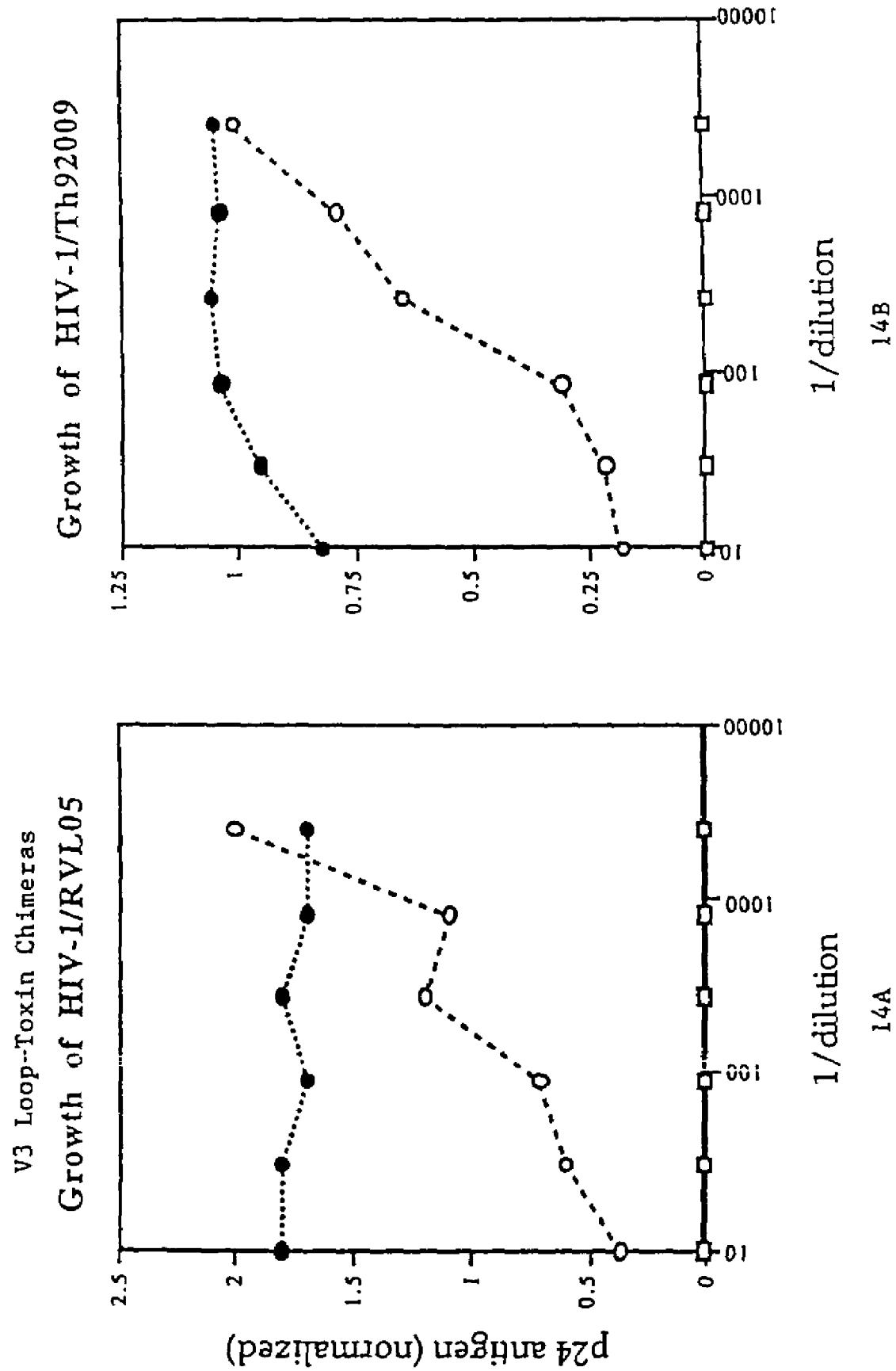

Because the sera taken from one of the rabbits immunized with ntPE-V3MN26 neutralized virus in the MT4 assay at a dilution of 1:400, this serum was used to evaluate activity against the clinical isolates. A serum sample taken at 24 weeks exhibited neutralizing activity against both a B and E subtype isolate (see FIG. 14). No neutralizing activity was seen with the pre-bleed sera from the same rabbit.

VI. Elicitation of IgA-Mediated Immune Response

Mucosal inoculation by a PE-like chimeric immunogen containing 26 amino acids of the V3 loop of gp120 of HIV-1 induced both a humoral and cell-mediated immune response against HIV-1. A toxic version of this chimera was capable of killing a human intestinal cell line, Caco-2, grown as confluent monolayers. A non-lethal form of the chimera was administered to mice either subcutaneously or at vaginal, rectal, gastric or nasal mucosal surfaces. Subsequent boostings were performed at these various mucosal surfaces of by subcutaneous administration. Measurement of MNgp120-specific antibodies in serum and saliva samples demonstrated both IgA and IgG responses in every group of mucosal and subcutaneous administration. These results demonstrate that the PE-like chimeric immunogens of this invention can enter epithelial cells, be trafficked similarly to native toxin, transport across an intact epithelial barrier and induce the production of both IgA and IgG antibodies.

A. PE-Like Chimeric Immunogens

PE-like chimeras used in these experiments are described in Example I. The structural gene encoding native (toxic) PE was modified to delete the Ib region and provide a unique PstI site for the insertion of 26 amino acid V3 loop sequences. Non-toxic versions of PE-V3 loop chimeras were prepared which lacked the glutamic acid residue at position 553 (ΔE553) and thus has no ADP-ribosylating activity. All PE-V3 loop chimeric proteins were expressed in *E. coli* BL21(XDE3) using the 17 promoter/T7 polymerase system. IPTG (1.0 mM for 90 min) was added to enhance protein expression. PE-V3 loop proteins were isolated from inclusion bodies and purified by successive rounds of anion exchange chromatography and a final gel filtration.

B. Cell-Based Studies

A toxic version of the *Pseudomonas* exotoxin (PE) chimera containing 26 amino acids of the V3 loop of MN gp120 (tPE-MN26) was applied to the apical surface of confluent monolayers of polarized Caco-2 cells. Caco-2 cells were cultured and maintained as previously described (W. Rubas et al. (1996) "Flux measurements across Caco-2 monolayers might predict transport in human large intestinal tissue" *J. Pharm. Sci.* 85:165-169) on prewetted (PBS, 15 min. outside and then inside) collagen-coated polycarbonate filter supports (Snapwells™). Culture media was changed every other day and confluent monolayers were used on day 25 post seeding and at passage 30-35. Toxic versions of PE and PE-V3 loop chimeras were added to the apical surface in culture media. After 24 h of continued incubation at 37° C., Caco-2 monolayers were washed thrice with PBS to remove serum esterase activities and incubated with calcein AM and ethidium homodimer to determine live/dead cell ratio (LIVE/DEAD® Eukolight kit; Molecular Probes, Inc., Eugene, Oreg.).

Figure 8:
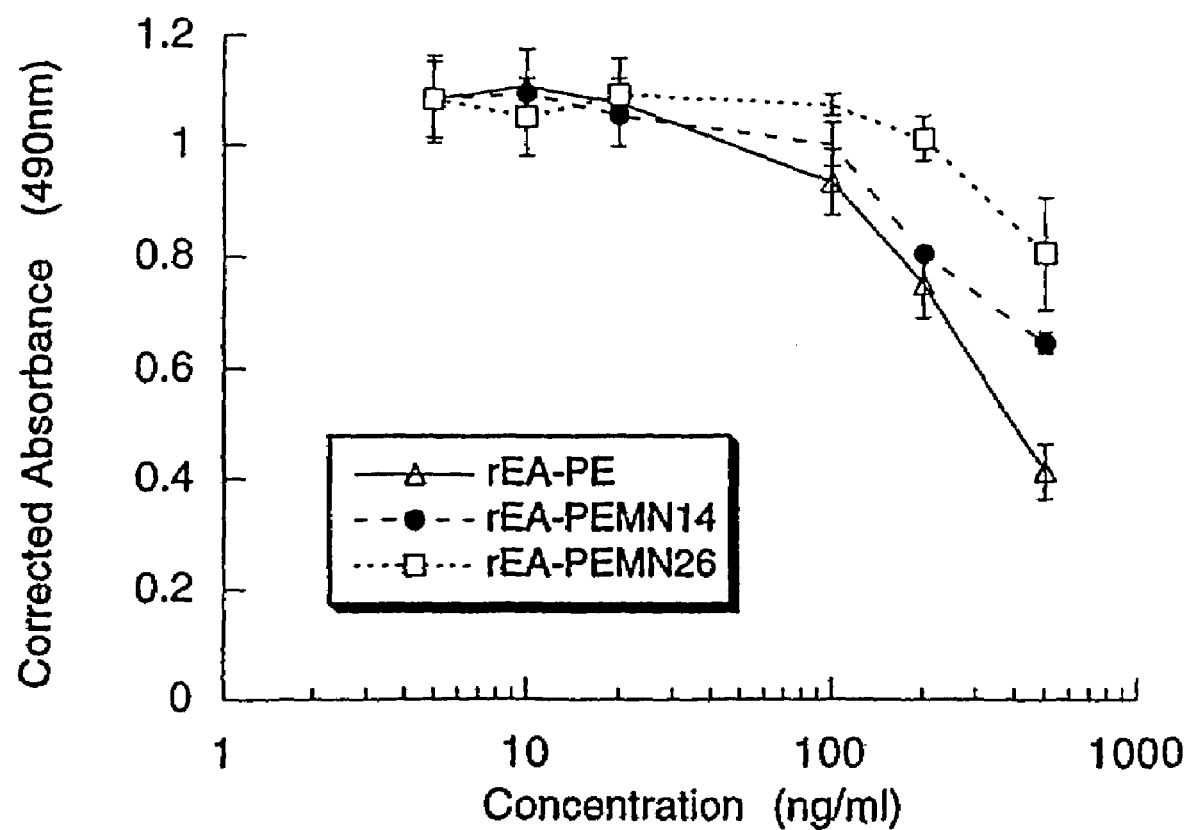
FIG. 8 demonstrates that PE-V3 loop chimeras are trafficked similarly to native PE. Confluent monolayers of Caco-2 cells were exposed apically to recombinant, enzymatically-active *Pseudomonas* exotoxin (rEA-PE). Cell killing produced by 24 h of exposure at various native PE (rEA-PE) concentrations were compared to that produced by similar treatment with enzymatically-active versions of PE chimeras containing either 14 or 26 amino acids of the V3 loop of HIV-1 MNgp120.

The chimera killed these intestinal epithelial cells with a potency similar to that of authentic PE (FIG. 8). Cell viability was measured as the ratio of live and dead cells.

A non-toxic (A553) chimera (ntPE-V3MN26) was used in all subsequent immunization studies to examine the ability of ntPE-V3MN26 to block the toxic actions of PE on Caco-2 monolayers (FIG. 8). Thus, the results of FIG. 8 show that the incorporation of 26 amino acids of the V3 loop of MNgp120 (ntPE-V3MN26) in place of the endogenous Ib loop of PE does not alter the ability of the PE chimera to be taken up and processed by polarized, confluent epithelial cells. This ability of the PE-V3 loop chimera to be taken up and processed by epithelial cells is important against a pathogen such as HIV-1 which can infect and alter the function of human intestinal epithelial cells. D. M. Asmuth et al. (1994) "Physiological effects of HIV infection on human intestinal epithelial cells: an in vitro model for HIV enteropathy" *AIDS* 8:205-211.

C. Immunization Protocols

Female balb-c mice were obtained from Simonsen at 6-8 weeks of age and quarantined for 2 weeks prior to study. Animals were placed into one of 6 groups which were inoculated 3 times at two week intervals. The animals were maintained on ad lib food and water. Animal groups were immunized as follows: (1) oral, oral, oral; (2) vaginal, vaginal, vaginal; (3) rectal, rectal, rectal; (4) vaginal, oral, oral; (5) rectal, oral, oral; and (5) subcutaneous, subcutaneous, subcutaneous. Each oral inoculation used 40 μg of PE-V3 loop chimera in 200 μl of PBS containing 0.05% Tween 20, 1 mg/ml BSA and 0.2 M NaHCO₃ (pH=8.1). All vaginal, rectal and subcutaneous inoculations contained 20 μg PE-V3 loop chimera in 20 μl of PBS containing 0.05% Tween 20.

D. Antibody Titers

Following intraperitoneal injection of 0.1 mg pilocarpine, mouse saliva (typically 50 μl) was collected using polypropylene Pasteur pipettes and placed into polypropylene tubes. Serum samples (100 μl) were obtained from periorbital bleeds using serum separator tubes. Collected serum and saliva samples were stored at −70° C. until analysis. A gp120-specific ELISA was performed using Costar 9018 E.I.A./R.I.A. plates coated with gp120. Following washing with PBST (PBS containing 0.05% Tween 20 and 0.01% thimerosal), plates were blocked with assay buffer (PBST containing 0.5% BSA). A subsequent washing was performed prior to serum or saliva sample introduction (100 μl/well). Bound immunoglobulins were tagged using biotinylated whole goat antibodies which selectively recognized either mouse IgA or mouse IgG (Amersham). A mouse monoclonal antibody denoted 1F12 (Genentech, Inc.) was used as a positive control for IgG assays. No gp120-specific mouse IgA was available as a positive standard. ExtrAvidin® peroxidase conjugate (Sigma), 2,2'-azino-bis(2-ethylbenzthiazoline-6-sulfonic acid (Sigma) and a phosphate-citrate buffer containing urea and hydrogen peroxide were used to quantitate bound antibody at 405 nm.

Figure 9:
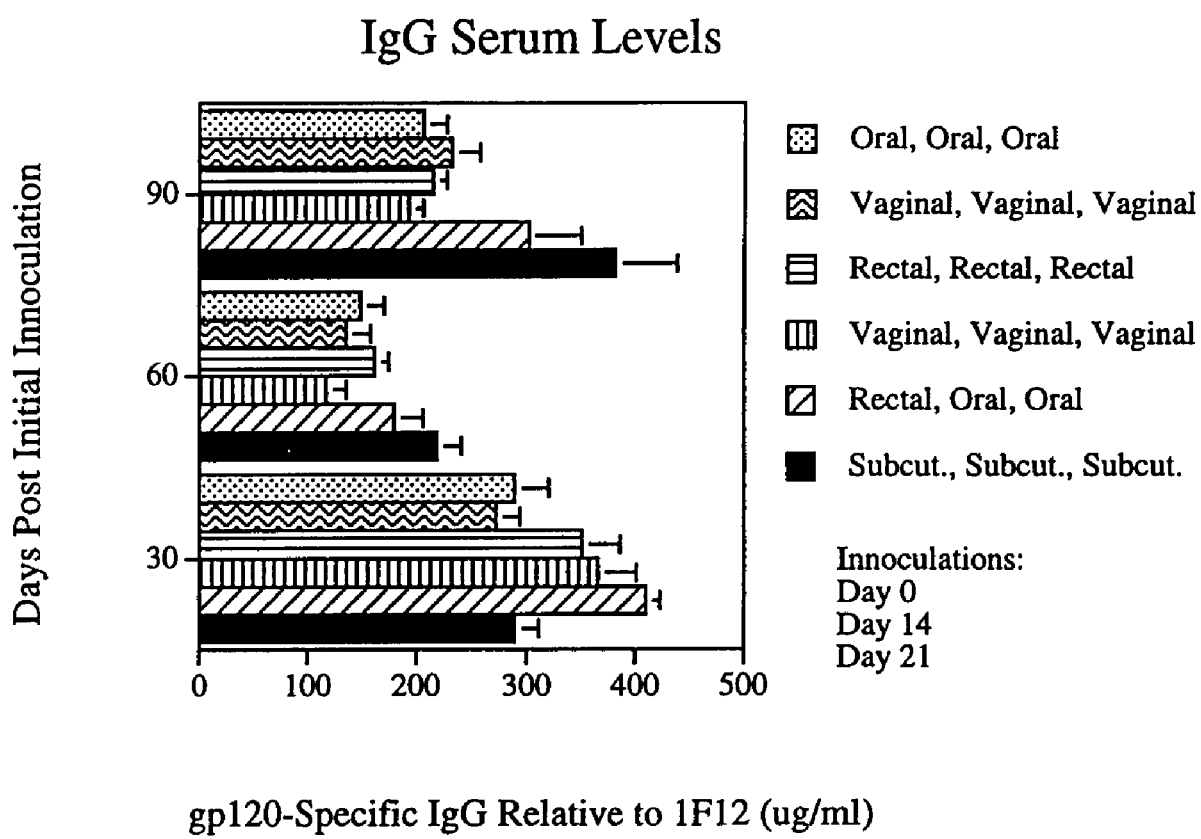
FIG. 9 demonstrates that PE-V3 loop chimeras induce a serum IgG response. A non-toxic (enzymatically inactive) V3 loop chimera containing 26 amino acids of the V3 loop of HIV-1 MNgp120 (PEMN26) was administered to rabbits through six different inoculation protocols. Serum samples drawn at the times described were assayed by ELISA for MNgp120-specific IgG using a monoclonal antibody (1F12) which recognizes the V3 loop of this protein for assay calibration.

Non-toxic PE-V3MN26 was delivered to balb-c mice in combinations of oral gavage, application to the vaginal mucosa, application to the rectal mucosa or by subcutaneous injection. Serum and saliva samples were collected one, two and three months after the initial inoculation from each dosing group and analyzed by ELISA to determine IgG and IgA antibody titers specific for MN gp120. Pre-immune saliva and serum samples showed no significant background reaction in these gp120-specific ELISAs. Measurable quantities of gp120-specific IgG were observed in the sera of all dosing groups (FIG. 9). Although the IgG response observed was initially greatest in the subcutaneous group, all groups ultimately demonstrated strong serum IgG responses. Groups that were exposed orally to the ntPE-V3MN26 also appeared to obtain an IgG response faster than those groups exposed only at the vaginal or rectal mucosa. Compared to a mouse-monoclonal $IgG_1$ which selectively recognizes the V3 loop of MNgp120, the highest measured levels in each of the groups of gp120-specific IgG were between 5-25 μg/ml sera.

Figure 10:
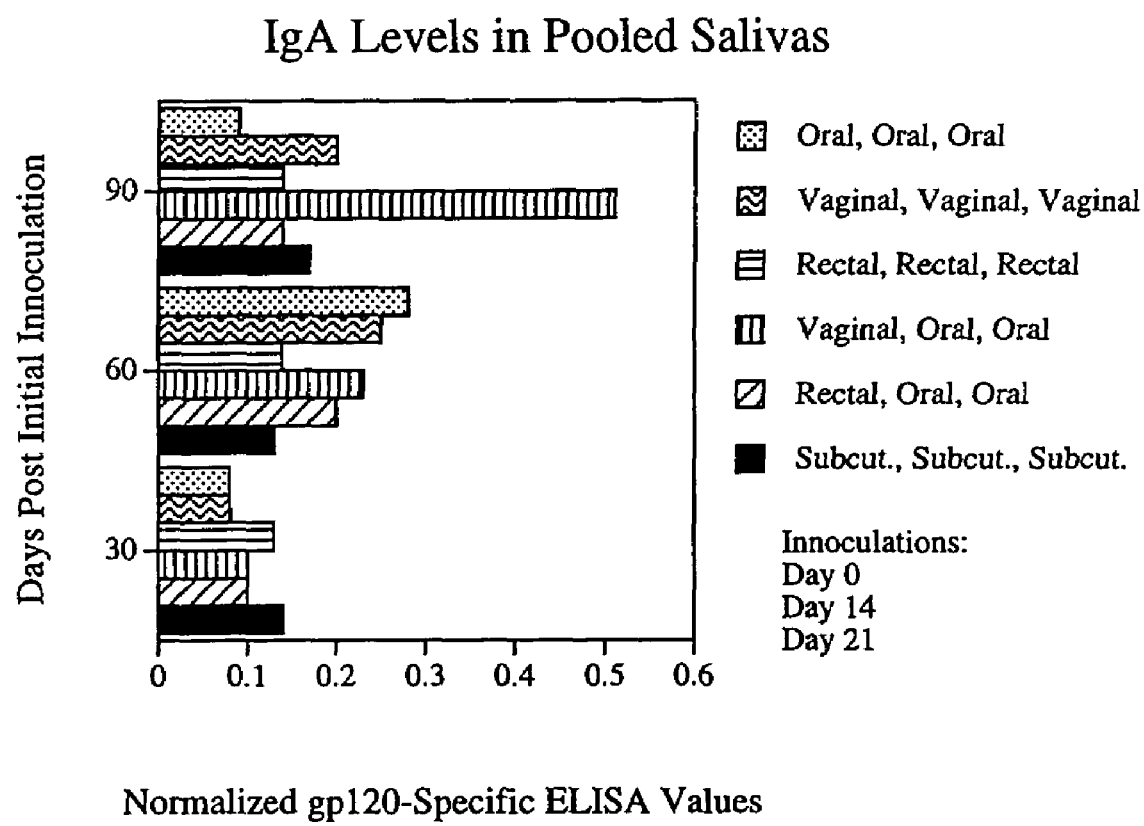
FIG. 10 shows that PE-V3 loop chimeras induce a salivary IgA response. A non-toxic (enzymatically inactive) V3 loop chimera containing 26 amino acids of the V3 loop of HIV-1 MNgp120 (PEMN26) was administered to rabbits through six different inoculation protocols. Saliva samples obtained following pilocarpine administration at the times described were assayed by ELISA for MNgp120-specific IgA. No gp120-specific IgA antibody was available for assay calibration. Values are reported as values normalized to a standardized positive sample.

IgA antibodies appear to contribute to resistance against both strict mucosal pathogens and invasive agents which go on to cause systemic disease after mucosal colonization. R. I. Walker et al. (1994) "New strategies for using mucosal vaccination to achieve more effective immunization" *Vaccine* 12:387-400. An ELISA was used to determine gp120-specific IgA levels in collected saliva samples as an index of mucosal antibody response. Since there is no MN gp120-specific monoclonal IgA available, values obtained by ELISA were only compared between groups and not characterized as absolute levels. Saliva samples from all 6 dosing groups contained gp120-specific IgA (FIG. 10). The strongest IgA response was observed in animals which received an initial vaginal dose and subsequent oral doses of PE-V3 loop chimera. It was interesting that animals which received only subcutaneous injections demonstrated IgA levels comparable to some of those observed in groups receiving only mucosal exposure of the chimera. This may be related to issues of the antibodies used in the IgA ELISA. Regardless, these results show that both mucosal and systemic immunity can be induced by mucosal immunization similar to that observed previously with oral immunization using pertussis toxin. M. J. Walker, et al. (1992) "Specific lung mucosal and systemic immune responses after oral immunization of mice with *Salmonella typhimurium* aro A, *Salmonella typhi* Ty21a, and invasive *Escherichia coli* expressing recombinant pertussis toxin S1 subunit" *Infect. Immun.* 60:4260.

HIV-1 subunit vaccines have been reported to only produce an IgG response following subcutaneous administration (M. B. Vasudevachari et al. (1992) "Envelope-specific antibodies in the saliva of individuals vaccinated with recombinant HIV-1 gp160" *J. Acquir. Immune Defic. Syndr.* 5:817-821) or both IgG and IgA following intramuscular injection (G. J. Gorse et al. (1996) "Salivary binding antibodies induced by human immunodeficiency virus type 1 recombinant gp120 vaccine" *Clin. Diagnostic Lab. Immunol.* 3:769-773.). Although those authors suggested that maximizing the production of mucosal antibodies will be important for an HIV-1 vaccine, it is unclear, however, if the IgA antibodies detected were secretory. It is likely that sIgA was the primary form of IgA in saliva samples and that dimeric IgA was the primary form in serum samples in those as well as the present studies. The IgA-binding reagent used presently was raised against serum IgA and thus may have provided a bias in IgA measurements. Thus the IgA levels measured in serum may only appear greater than saliva levels due to a lower affinity for sIgA than dimeric IgA. The IgA values given in the present study, therefore, are only presented on a relative scale.

A number of factors released by Th1 and Th2 cells have been shown to regulate IgA responses (J. R. McGhee et al. (1993) "New perspectives in mucosal immunity with emphasis on vaccine development" *Seminars in Hematology*. 30:3-15). For example, in the presence of IL-5, IL-2 synergizes with TGF-β to augment IgA synthesis, leading to the prospect of pharmacologically manipulating the immune response. The form of antigen presentation, however, is dictated significantly by the fate of the immunogen. Epithelial cells at mucosal surfaces, which have the LRP receptor to bind and internalize ntPE-V3MN26, have been shown to express MHC class II proteins and class II can efficiently reach the surface of cells for antigen presentation from a lysosomal origin (V. G. Brachet et al. (1997) "Ii chain controls the transport of major histocompatibility complex class II molecules to and from lysosomes" *J. Cell Biol.* 137:51-65). Thus, ntPE-V3MN26 can be delivered by MHC class II structures onto the cell surface of epithelial cells. Alternatively, if the immunogen crosses the mucosal barrier and reaches a professional antigen presentation cell in the underlying lamina propria in an intact form, it should induce a Th2 response and result in a MHC class I-restricted antigen presentation.

VII. Memory Response Elicited by Mucosal Administration of Chimeric Immunogen

Mucosal administration of ntPE-V3MN26 produced a significant memory response characterized by combination of serum IgG isotypes of both Th1 and Th2 pathways. Since the Th2 response has been proposed to be advantageous for neutralizing viruses and the cytotoxic immune responses associated with Th1 events may be required for effective immune responses against intracellular viruses (J. R. McGhee et al. (1994) *Reprod. Fertil. Dev.* 6:369-379), these results suggest that the mucosal immunization with ntPE-V3MN26 provided the types of responses desired for protection against HIV-1 infection (G. L. Ada et al. (1997) *AIDS Res. Hum. Retrovinises* 13:205-210.

A. Materials and Methods

1. Reagents

The structure and preparation of the ntPE-V3MN26 used in these studies is described herein. MNgp120 and the 1F12 monoclonal antibody recognizing the V3 loop of MNgp120 were prepared at Genentech, Inc. (South San Francisco, Calif.). Biotin-labeled goat antibodies raised against either mouse IgG or mouse IgA were purchased from Amersham Life Sciences (Arlington Heights, Ill.). Biotinylated rat antibodies recognizing mouse $IgG_1$, $IgG_{2a}$, $IgG_{2b}$, $IgG_3$ and IgE were obtained from Pharmingen (San Diego, Calif.).

2. Immunization Protocols and Samples Collection

Female BALB/c mice were obtained at 6-8 weeks of age and quarantined for 2 weeks prior to study and maintained throughout the study on ad lib food and water. Animals were randomly assigned to groups (n=6) which received combinations of oral, vaginal, rectal or subcutaneous dosings. Oral inoculations were performed by oral gavage of 200 μl of PBS containing 0.05% Tween 20, 1 mg/ml BSA, 0.2 M $NaHCO_3$ (final pH=8.1) and 40 μg of ntPE-V3MN26. Vaginal, rectal, and subcutaneous inoculations contained 20 μg ntPE-V3MN26 in 20 µl of PBS containing 0.05% Tween 20. Mouse saliva (typically 50-100 µl) was collected over approximately 10 min using polypropylene Pasteur pipettes following hypersalivation induced by intraperitoneal injection of 0.1 mg pilocarpine per animal. Serum samples (100 µl) were obtained from periorbital bleeds using serum separator tubes. Collected serum and saliva samples were stored at −70° C. until analysis.

In a separate study, mice were subcutaneously injected with 20 µg ntPE-V3MN26 or 20 µg ntPE and boosted at 2 and 7 weeks. One set of animals receiving ntPE-V3MN26 (n=3) and the animals receiving ntPE (n=2) were simultaneously dosed with 40 µl of Freund's complete adjuvant initially and 40 µl of Freund's incomplete adjuvant at weeks 2 and 7. A set of animals (n=3) dosed with 20 µg of ntPE-V3MN26 formulated in 40 µl of normal saline served as a control. Serum samples (100 µl) were obtained on a weekly basis and stored as described above.

3. Measurement of Antibody Responses

Anti-gp120-specific antibodies were measured by enzyme-linked immunosorbent assay (ELISA). Briefly, Costar 9018 E.I.A./R.I.A. 96-well plates were coated with 1 µg/well of MNgp120, washed thrice with PBS containing 0.05% Tween 20 (v/v) and then blocked overnight at 4° C. with PBS containing 1% BSA. After washing with PBS/Tween 20, plates were incubated with dilutions of serum or saliva samples (diluted with PBS/Tween 20 containing 0.1% BSA). The plates were incubated for 2 h at room temperature with gentle agitation, then washed thrice with PBS/Tween 20 and incubated with a biotin-conjugated goat anti-mouse IgA or IgG or, to determine IgG subclass or IgE responses, with biotin-conjugated rat anti-mouse IgG1, IgG2a, IgG2b, IgG3, or IgE for 1 h using the same incubation conditions. After washing with PBS/Tween 20, horseradish peroxidase-conjugated streptavidin was added. Bound antibodies were visualized by ExtrAvidin® peroxidase conjugate (Sigma), 2,2'-azino-bis(2-ethylbenzthiazoline-6-sulfonic acid (Sigma) and a phosphate-citrate buffer containing urea and hydrogen peroxide were used to quantitate bound antibody at 405 nm.

B. Results

1. IgA Antibody Responses to ntPE-V3MN26

Figure 11:
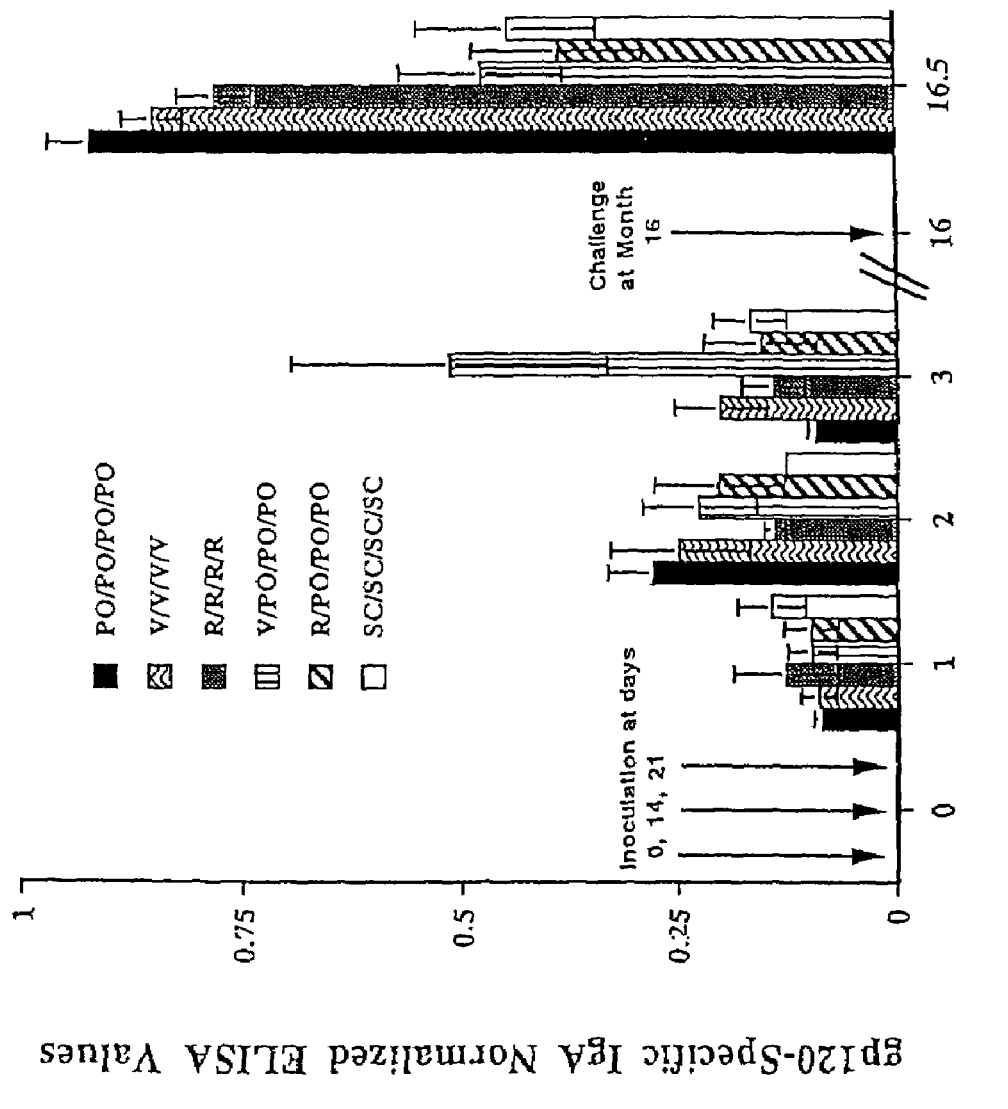
FIG. 11 shows relative levels of salivary IgA following mucosal or systemic inoculation with ntPE-V3MN26. MNgp120 specific IgA antibodies were measured by ELISA in saliva samples, normalized against a strongly positive sample and reported on an arbitrary scale of one antigen-specific IgA unit.

Animals were inoculated (n=6/group) by a variety of routes with ntPE-V3MN26 followed by 2 boosts on days 14 and 21 and then at month 16. Animals received ntPE-V3MN26 either orally (PO), vaginally (V), rectally (R), vaginally and orally (V/PO), rectally and orally (R/PO), or subcutaneously (SC). Saliva samples collected at 30, 60 and 90 days and then again at 16.5 months were analyzed for antigen-specific IgA (FIG. 11). Without an anti-V3 loop IgA antibody to standardize the assays, responses were normalized against one strongly positive sample. Values were reported on an arbitrary scale of antigen-specific IgA units. All dosing groups demonstrated comparable salivary IgA responses at 30 and 60 days. By 90 days, the strongest salivary IgA response was observed in the group which received an initial vaginal dose and subsequent oral boosts. At 16.5 months the all oral, all vaginal and all rectal groups showed the greatest levels of antigen-specific salivary IgA. Responses of the combined mucosal inoculation groups (vaginal/oral and rectal/oral) were comparable to those observed in the group dosed subcutaneously.

To insure that these salivary IgA responses reflected antigen-specific binding and not a non-specific binding to salivary components, pre-immune saliva samples were evaluated and a study was performed in which a mixture of V3 loop peptide and ntPE was administered to mice. The studies showed that undiluted pre-immune saliva samples did not demonstrate a measurable background in the ELISA format. Also, animals dosed simultaneously with ntPE and an unconjugated V3 loop constrained by a disulfide bond did not have measurable MNgp120-specific IgA levels. These results indicate that there was little or no non-specific cross-reactivity in the ELISA.

No detectable antigen-specific serum IgA responses were observed in any of the dosing groups at the 1, 2 or 3 month sampling times. However, at 16.5 months, sera collected from all groups demonstrated antigen-specific IgA (Table 1). It is possible that the ability to detect serum IgA at this time may have been due to a heightened total immune response rather than a specific stimulation. Interestingly, the relative serum IgA levels did not correlate with salivary IgA levels. For example, rectal/oral combination inoculations yielded one of the weaker memory salivary IgA responses but the strongest memory serum IgA response (Table 1, FIG. 11). The all oral, all vaginal or all rectal groups, which provided the greatest salivary IgA responses at 16.5 months had some of the weakest serum IgA responses at this time. Unlike mucosal administration of ntPE-V3MN26 where opposing levels in saliva and serum were the norm, subcutaneous inoculations of ntPE-V3MN26 produced a moderate IgA response in both the saliva and serum of mice (Table 1, FIG. 11). Whatever the stimulus of IgA production, the antigen-specific serum IgA levels were transient. At the 22 month sampling, just two animals of the rectal/oral group represented the only positives for measurable serum IgA recognizing MNgp120. No other groups, even the subcutaneous injection group, showed any detectable serum IgA levels at this time point.

TABLE 1

Immunization with ntPE-V3MN26 stimulates the production of antigen-specific serum IgA and salivary IgG in Mice

| Immunization schedule[a] | Serum IgA[b] (arbitrary units) | Salivary IgG[c] (µg/ml) |
|---|---|---|
| PO/PO/PO/PO | 0.233 ± 0.074 | 10.9 ± 2.2 |
| V/V/V/V | 0.172 ± 0.061 | 9.52 ± 1.6 |
| R/R/R/R | 0.178 ± 0.042 | 9.93 ± 1.7 |
| V/PO/PO/PO | 0.160 ± 0.021 | 9.90 ± 1.3 |
| R/PO/PO/PO | 0.450 ± 0.128 | 11.0 ± 0.49 |
| SC/SC/SC/SC | 0.273 ± 0.078 | 7.1 ± 0.63 |

[a]Immunizations were performed at days 0, 14, 21 and at month 16 to animals either orally (PO) vaginally (V), rectally (R) or subcutaneously (SC).
[b]MNgp120-specific IgA levels were measured by ELISA at 16.5 months and normalized against a single sample standard and reported in arbitrary units.
[c]MNgp120-specific IgG levels were measured by ELISA at 16.5 months and calibrated against a mouse monoclonal antibody (1F12) which recognizes the V3 loop of the protein.

2. IgG Antibody Responses to ntPE-V3MN26

Serum and salivary antigen-specific IgG responses, measured by ELISA, were standardized using a mouse monoclonal antibody (1F12) which recognizes the V3 loop of MNgp120. The assay was linear over the range of 0.05-2.5 µg for 1F12 and pre-immune sera and salivas were negative in the ELISA format. Although the IgG response produced by an initial inoculation followed by two boosts was ultimately greatest in the subcutaneous injection group, all mucosal inoculation groups demonstrated strong serum IgG responses at 30, 60 and 90 days (FIG. 12). Two weeks after an ntPE-V3MN26 boost at month 16 the subcutaneous injection group had the highest serum IgG memory response. All mucosal groups also showed strong memory responses at this time (FIG. 12). However, by month 22 antigen-specific serum IgG titers had decreased in all groups.

3. Comparison of Serum and Saliva IgG and IgA Levels

Previous studies have suggested that serum IgG can transudate onto mucosal surfaces, possibly providing some form of immune protection. M. B. Vasudevachari et al. (1992) *J. Acquir. Immune Defic. Syndr.* 5:817-821. Others have not been able to demonstrate such a transudative event. E.-L. Johansson et al. (1998) *Infect. Immun.* 66:514-520. In these studies, antigen-specific IgG was not observed in saliva samples at months 1, 2 and 3 but rose to detectable levels following a boost at month 16 (Table 1). All mucosally dosed animal groups had comparable salivary IgG responses at this time which were greater than that observed for the animals receiving subcutaneous ntPE-V3MN26 (Table 1). This lack of correlation between relative serum and saliva levels of antigen-specific IgG (FIG. 12, Table 1) suggests a separation of the serum and salivary IgG pools resulting from this memory response. Thus, it appears that the IgG present in saliva in the studies may have resulted, to a significant extent, from local antibody production rather than a "spill-over" from circulating serum antibodies.

4. Serum IgG Isotype Responses to ntPE-V3MN26

In mice, induction of a Th1 response typically leads to the production of IgG2a and IgG3 by B cells while a Th2 response results in IgG1 and possibly IgE production. A. K. Abbas et al. (1996) *Nature* 383:787-793. The development of either a Th1 or Th2 response is driven by specific cytokines such as interferon-γ and IL-4. Introduction of ntPE-V3MN26 either systemically through subcutaneous injection or via application at oral, vaginal or rectal tissues led to the development of an antigen-specific serum IgG response. The IgG isotype population of these sera samples was investigated and it was found that the MNgp120-specific response was dominated (~55%) by IgG1. Lesser and comparable amounts of antigen-specific IgG2a (~20%) and IgG2b (~20%) were found along with low amounts (~5%) of IgG3. No antigen-specific IgE was detected. These results suggest that subcutaneous administration of ntPE-V3MN26 induces both Th1 and Th2 responses in BALB/c mice with the Th2 phenotype dominating.

VIII. Evaluation of ntPE-V3MN26 as an Adjuvant

Figure 13:
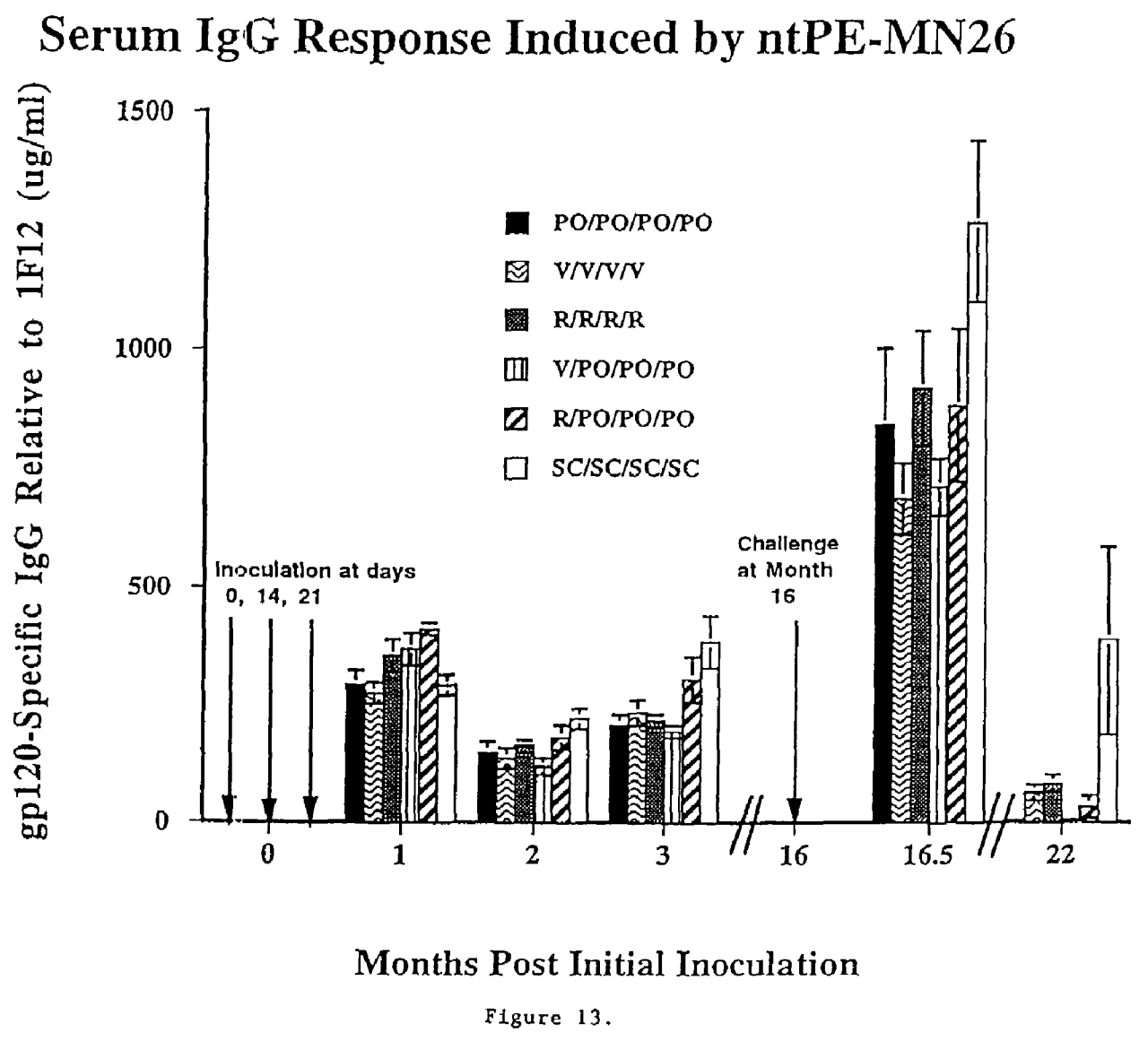

Adjuvants can act to facilitate the presentation of an antigen and/or activate the immune response at the site of inoculation. F. R. Vogel et al. (1995) *A compendium of vaccine adjuvants and excipients,* p. 141-228. In M. F. Powell, and M. J. Newman (ed.), VACCINE DESIGN: THE SUBUNIT AND ADJUVANT APPROACH, vol. 6. Plemun Press, New York. Recognized as one of the most potent adjuvants available, Freund's adjuvant is a mixture of mineral oil, surfactant and *Mycobacterium tuberculosis.* A study to assess the efficiency of serum IgG induction by ntPE-V3MN26 was performed by injecting mice subcutaneously with ntPE-V3MN26 and Freund's complete adjuvant initially, boosting with ntPE-V3MN26 and incomplete adjuvant after 14 and 49 days, and then comparing IgG serum responses to those of animals receiving ntPE-V3MN26 without Freund's adjuvant (FIG. 13). Animals receiving the same subcutaneous dosing regime of ntPE-V3MN26 with normal saline instead of Freund's adjuvant exhibited approximately one-third the antigen-specific immune response that observed in animals receiving this chimera along with Freund's adjuvant. The level of response to ntPE-V3MN26 over this time frame was similar to that observed in the subcutaneous injection group graphed in FIG. 12 at months 1, 2 and 3, suggesting a fairly consistent outcome for this form of chimera delivery. A control where the Freund's adjuvant regimen was injected along with a non-toxic PE which lacked the V3 loop of MNgp120 demonstrated the specificity of the immune response being measured (FIG. 13).

The present invention provides *Pseudomonas* exotoxin A-like chimeric immunogens and methods of evoking an immune response. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A non-toxic *Pseudomonas* exotoxin A-like chimeric immunogen comprising in sequence: (1) a cell recognition domain comprising domain 1a of *Pseudomonas* exotoxin A (PE); (2) a translocation domain comprising a translocation domain of PE wherein the translocation domain is at least 95% identical to SEQ ID NO:2 from amino acid position 280 to amino acid position 344 and serves to translocate the instant chimeric immunogen to the cytosol of the cell; (3) an epitope presenting domain of between 5 and 350 amino acids in length that comprises one cysteine-cysteine loop wherein the loop encodes an epitope of a pathogen and wherein the epitope is non-native to PE domain Ib; (4) an endoplasmic reticulum (ER) retention domain wherein the ER domain is capable of effecting translocation to the endoplasmic reticulum of the cell and wherein the ER retention domain lacks ADP ribosylation activity.

2. The immunogen of claim 1, wherein the translocation domain is domain II of PE.

3. The immunogen of claim 1 wherein the translocation domain comprises the amino acid sequence of SEQ ID NO:2, from the amino acid at position to 280 to the amino acid at position 364.

4. The immunogen of claim 1, wherein the ER retention domain is domain III of PE having a deletion which eliminates ADP ribosylation activity.

5. The immunogen of claim 1, wherein the translocation domain comprises a translocation domain of PE wherein the translocation domain is at least 98% identical to SEQ ID NO:2 from amino acid position 280 to amino acid position 344.

6. The immunogen of claim 1 wherein the ER retention sequence comprises KDEL (SEQ ID NO:13) or REDL (SEQ ID NO:12).

7. The immunogen of claim 1, wherein the amino acid sequence of the ER retention domain is at least 95% identical to the amino acid sequence of SEQ ID NO:2 spanning amino acid positions from 400 to 613 thereof, wherein the ER retention domain has a deletion of the amino acid at position 553 of SEQ ID NO:2 and, optionally, a deletion of the lysine at position 613 of SEQ ID NO:2.

8. The immunogen of claim 1, wherein the translocation domain comprises the amino acid sequence of SEQ ID NO:2 at position 279 and the amino acid at position 279 is arginine.

9. A non-toxic *Pseudomonas* exotoxin A-like chimeric immunogen comprising in sequence: (1) a cell recognition domain of between 10 and 1500 amino acids that binds to a cell surface receptor of a mammal; (2) a translocation domain comprising a translocation domain of PE wherein the translocation domain is at least 95% identical to SEQ ID NO:2 from amino acid position 280 to amino acid position 344 and serves to translocate the instant chimeric immunogen to the cytosol of the cell; (3) an epitope presenting domain of between 5 and 350 amino acids in length that comprises one cysteine-cysteine loop wherein the loop encodes an epitope of a pathogen and wherein the epitope is non-native to PE domain Ib: (4) an endoplasmic reticulum (ER) retention domain wherein the ER domain is capable of effecting translocation to the endoplasmic reticulum of the cell and comprises the amino acid sequence REDLK (SEQ ID NO:11).

10. A non-toxic *Pseudomonas* exotoxin A-like chimeric immunogen comprising in sequence: (1) a cell recognition domain of between 10 and 1500 amino acids that binds to a cell surface receptor of a cell from a mammal; (2) a translocation domain comprising a translocation domain of PE wherein the translocation domain is at least 95% identical to SEQ ID NO:2 from amino acid position 280 to amino acid position 344 and serves to translocate the instant chimeric immunogen to the cytosol of the cell; (3) an epitope presenting domain of between 5 and 350 amino acids in length that comprises one cysteine-cysteine loop wherein the loop encodes an epitope of a pathogen and wherein the epitope is non-native to PE domain Ib and wherein the cysteine-cysteine loop of the pathogen is located within PE domain Ib in place of amino acid residues 372 to 379, inclusive, of SEQ ID NO:2; (4) an endoplasmic reticulum (ER) retention domain wherein the ER domain is capable of effecting translocation to the endoplasmic reticulum of the cell.

11. The immunogen of claim 10, wherein the cell recognition domain is domain I a of PE and the translocation domain is domain II of PE.

12. The immunogen of claim 10 wherein the cell recognition domain is domain Ia of PE.

* * * * *